(12) United States Patent
Sliwkowski

(10) Patent No.: US 6,949,245 B1
(45) Date of Patent: Sep. 27, 2005

(54) HUMANIZED ANTI-ERBB2 ANTIBODIES AND TREATMENT WITH ANTI-ERBB2 ANTIBODIES

(75) Inventor: Mark Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 215 days.

(21) Appl. No.: 09/602,812

(22) Filed: Jun. 23, 2000

Related U.S. Application Data
(60) Provisional application No. 60/141,316, filed on Jun. 25, 1999.

(51) Int. Cl.$^7$ .................. A61K 39/395; C07K 16/28; C07K 16/30

(52) U.S. Cl. .................. 424/143.1; 424/130.1; 424/133.1; 424/135.1; 424/136.1; 424/138.1; 424/141.1; 424/142.1; 424/172.1; 424/174.1; 424/178.1; 424/800; 424/801

(58) Field of Search .................. 424/143.1, 130.1, 424/133.1, 135.1, 136.1, 138.1, 141.1, 142.1, 172.1, 174.1, 178.1, 800, 801, 152.1, 155.1, 137.1

(56) References Cited

U.S. PATENT DOCUMENTS

| | | |
|---|---|---|
| 4,753,894 A | 6/1988 | Frankel et al. |
| 4,935,341 A | 6/1990 | Bargmann et al. |
| 4,943,533 A | 7/1990 | Mendelsohn et al. |
| 4,968,603 A | 11/1990 | Slamon et al. |
| 4,975,278 A | 12/1990 | Senter et al. |
| 5,169,774 A | 12/1992 | Frankel et al. |
| 5,183,884 A | 2/1993 | Kraus et al. |
| 5,288,477 A | 2/1994 | Bacus |
| 5,359,046 A | 10/1994 | Capon et al. |
| 5,367,060 A | 11/1994 | Vandlen et al. |
| 5,401,638 A | 3/1995 | Carney et al. |
| 5,464,751 A | 11/1995 | Greene et al. |
| 5,480,968 A | 1/1996 | Kraus et al. |
| 5,514,554 A | 5/1996 | Bacus |
| 5,571,894 A | 11/1996 | Wels et al. |
| 5,578,482 A | 11/1996 | Lippman et al. |
| 5,587,458 A | 12/1996 | King et al. |
| 5,604,107 A | 2/1997 | Carney et al. |
| 5,641,869 A | 6/1997 | Vandlen et al. |
| 5,648,237 A | 7/1997 | Carter |
| 5,663,144 A | 9/1997 | Greene et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A * | 3/1998 | Hudziak et al. ......... 424/130.1 |
| 5,726,023 A | 3/1998 | Cheever et al. |
| 5,728,687 A | 3/1998 | Bissery |
| 5,747,261 A | 5/1998 | King et al. |
| 5,770,195 A | 6/1998 | Hudziak et al. |
| 5,772,997 A | 6/1998 | Hudziak et al. |
| 5,776,427 A | 7/1998 | Thorpe et al. |
| 5,783,186 A | 7/1998 | Arakawa et al. |
| 5,783,404 A | 7/1998 | Koski |
| 5,801,005 A | 9/1998 | Cheever et al. |
| 5,804,396 A | 9/1998 | Plowman |
| 5,821,337 A | 10/1998 | Carter et al. |
| 5,824,311 A | 10/1998 | Greene et al. |
| 5,834,229 A | 11/1998 | Vandlen et al. |
| 5,837,243 A | 11/1998 | Deo et al. |
| 5,837,523 A | 11/1998 | Greene et al. |
| 5,840,525 A | 11/1998 | Vandlen et al. |
| 5,846,538 A | 12/1998 | Cheever et al. |
| 5,846,749 A | 12/1998 | Slamon et al. |
| 5,856,089 A | 1/1999 | Wang et al. |
| 5,856,110 A | 1/1999 | Vandlen et al. |
| 5,859,206 A | 1/1999 | Vandlen et al. |
| 5,869,445 A | 2/1999 | Cheever et al. |
| 5,876,712 A | 3/1999 | Cheever et al. |
| 5,877,305 A | 3/1999 | Huston et al. |
| 5,882,864 A | 3/1999 | An et al. |
| 5,908,835 A | 6/1999 | Bissery |
| 5,910,486 A | 6/1999 | Curiel et al. |
| 5,922,845 A | 7/1999 | Deo et al. |
| 5,925,519 A | 7/1999 | Jensen et al. |
| 5,939,531 A | 8/1999 | Wels et al. |
| 5,968,511 A | 10/1999 | Akita et al. |
| 5,977,322 A | 11/1999 | Marks et al. |
| 5,985,553 A | 11/1999 | King et al. |
| 5,994,071 A | 11/1999 | Ross et al. |
| 6,015,567 A | 1/2000 | Hudziak et al. |
| 6,028,059 A | 2/2000 | Curiel et al. |
| 6,054,297 A | 4/2000 | Carter et al. |
| 6,054,561 A | 4/2000 | Ring |
| 6,096,873 A | 8/2000 | Schaefer et al. |
| 6,123,939 A | 9/2000 | Shawver et al. |
| 6,127,526 A | 10/2000 | Blank |
| 6,165,464 A | 12/2000 | Hudziak et al. |
| 6,214,388 B1 | 4/2001 | Benz et al. |

(Continued)

FOREIGN PATENT DOCUMENTS

| | | |
|---|---|---|
| EP | 599274 | 6/1994 |
| EP | 0616812 A1 | 9/1994 |
| EP | 656367 | 6/1995 |

(Continued)

OTHER PUBLICATIONS

Maurer, C.S. et al. Human Pathology, 29(8): 771–777, 1998.*

Bast, R.C. et al. Cancer Molecular Biology, 1(2): 87–93, 1994*

Shackney, S.E. et al., Clinical Cancer Research, 4(4): 913–928, 1998.*

(Continued)

Primary Examiner—Alana M. Harris
Assistant Examiner—Anne L. Holleran
(74) Attorney, Agent, or Firm—Wendy M. Lee

(57) ABSTRACT

The present application describes humanized anti-ErbB2 antibodies and methods for treating cancer with anti-ErbB2 antibodies, such as humanized anti-ErbB2 antibodies.

24 Claims, 14 Drawing Sheets

U.S. PATENT DOCUMENTS

| | | |
|---|---|---|
| 6,267,958 B1 | 7/2001 | Andya et al. |
| 6,270,765 B1 | 8/2001 | Deo et al. |
| 6,333,169 B1 | 12/2001 | Hudziak et al. |
| 6,333,348 B1 | 12/2001 | Vogel et al. |
| 6,333,398 B1 | 12/2001 | Blank |
| 6,339,142 B1 | 1/2002 | Basey et al. |
| 6,358,682 B1 | 3/2002 | Jaffee et al. |
| 6,387,371 B1 | 5/2002 | Hudziak et al. |
| 6,395,272 B1 | 5/2002 | Deo et al. |
| 6,399,063 B1 | 6/2002 | Hudziak et al. |
| 6,403,630 B1 | 6/2002 | Dannenberg et al. |
| 6,407,213 B1 | 6/2002 | Carter et al. |
| 6,417,168 B1 | 7/2002 | Greene et al. |
| 6,417,335 B1 | 7/2002 | Basey et al. |
| 6,458,356 B1 | 10/2002 | Arakawa et al. |
| 6,489,447 B1 | 12/2002 | Basey et al. |
| 6,512,097 B1 | 1/2003 | Marks et al. |
| 6,582,919 B2 | 6/2003 | Danenberg |
| 6,627,196 B1 | 9/2003 | Baughman et al. |
| 6,685,940 B2 | 2/2004 | Andya et al. |
| 6,719,971 B1 | 4/2004 | Carter et al. |
| 6,797,814 B2 | 9/2004 | Blank |
| 6,800,738 B1 | 10/2004 | Carter et al. |
| 2002/0076695 A1 | 6/2002 | Ross |
| 2002/0141993 A1 | 10/2002 | Ashkenazi et al. |
| 2002/0155527 A1 | 10/2002 | Stuart et al. |
| 2002/0192211 A1 | 12/2002 | Hudziak et al. |
| 2003/0059790 A1 | 3/2003 | Jaffee et al. |
| 2003/0103973 A1 | 6/2003 | Rockwell et al. |
| 2003/0108545 A1 | 6/2003 | Rockwell et al. |
| 2003/0152987 A1 | 8/2003 | Cohen et al. |
| 2003/0211530 A1 | 11/2003 | Danenberg |

FOREIGN PATENT DOCUMENTS

| | | |
|---|---|---|
| EP | 412116 | 11/1995 |
| EP | 494135 | 4/1996 |
| EP | 502812 | 8/1996 |
| EP | 711565 | 8/1998 |
| EP | 554441 | 1/1999 |
| EP | 1006194 | 6/2000 |
| EP | 444181 | 10/2001 |
| JP | 3-240498 | 10/1991 |
| JP | 5-117165 | 5/1993 |
| JP | 5-170667 | 7/1993 |
| JP | 5-213775 | 8/1993 |
| JP | 5-317084 | 12/1993 |
| JP | 95006982 B2 | 1/1995 |
| JP | 7-59588 | 3/1995 |
| JP | 2761543 B2 | 6/1998 |
| JP | 2895105 B2 | 5/1999 |
| WO | WO 87/07646 | 12/1987 |
| WO | WO 89/06692 | 7/1989 |
| WO | WO 89/10412 | 11/1989 |
| WO | WO 90/14357 | 11/1990 |
| WO | WO 91/02062 | 2/1991 |
| WO | WO 91/05264 | 4/1991 |
| WO | WO 92/10573 | 6/1992 |
| WO | WO 92/20798 | 11/1992 |
| WO | WO 93/03741 | 3/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 94/00136 | 1/1994 |
| WO | WO 94/22478 | 10/1994 |
| WO | WO 94/28127 | 12/1994 |
| WO | WO 95/16051 | 6/1995 |
| WO | WO 95/17507 | 6/1995 |
| WO | WO 95/28485 | 10/1995 |
| WO | WO 96/07321 | 3/1996 |
| WO | WO 96/16673 | 6/1996 |
| WO | WO 96/18409 | 6/1996 |
| WO | WO 96/40789 | 12/1996 |
| WO | WO 97/00271 | 1/1997 |
| WO | WO 97/04801 | 2/1997 |
| WO | WO 97/20858 | 6/1997 |
| WO | WO 97/27848 | 8/1997 |
| WO | WO 97/35885 | 10/1997 |
| WO | WO 97/38731 | 10/1997 |
| WO | WO 98/02463 | 1/1998 |
| WO | WO 98/02540 | 1/1998 |
| WO | WO 98/02541 | 1/1998 |
| WO | WO 98/16628 | 4/1998 |
| WO | WO 98/17797 | 4/1998 |
| WO | WO 98/18489 | 5/1998 |
| WO | WO 98/33914 | 8/1998 |
| WO | WO 98/45479 | 10/1998 |
| WO | WO 99/31140 | 6/1999 |
| WO | WO 99/39729 | 8/1999 |
| WO | WO 99/55367 | 11/1999 |
| WO | WO 00/61145 | 10/2000 |
| WO | WO 00/61185 | 10/2000 |
| WO | WO 00/69460 | 11/2000 |
| WO | WO 00/78347 | 12/2000 |
| WO | WO 01/00238 A1 | 1/2001 |
| WO | WO 01/00244 A2 | 1/2001 |
| WO | WO 01/00245 | 1/2001 |
| WO | WO 01/05425 | 1/2001 |
| WO | WO 01/09187 | 2/2001 |
| WO | WO 01/15730 A1 | 3/2001 |
| WO | WO 01/20033 | 3/2001 |
| WO | WO 01/21192 | 3/2001 |
| WO | WO 01/32155 | 5/2001 |

OTHER PUBLICATIONS

Brabender, J. et al. Clinical Cancer Research, 7(7): 1850–1855, 2001.*

Zhang, H. et al. Experimental and Molecular Pathology, 67: 15–25, 1999.*

Suzuki, T. et al. Oncology, 52(5): 385–391, 1995.*

Dillman et al., J Clin Onco vol. 12, No. 7, pp. 1497–1515, Jul. 1997.*

Dermer Bio/Technology, vol. 12, p. 320, Mar. 1994.*

Jardines et al., Pathobiology, vol. 61, pp. 268–282, 1993.*

Grim et al., Am. J. Respir. Cell Mol. Biol., vol. 15, pp. 348–354, Sep. 1996.*

Kern et al., Am. J. Respir. Cell Mol. Biol., vol. 9, pp. 448–454, 1993.*

Baselga et al., Oncology, Suppl. 2, Mar. 1997, pp. 43–48.*

Schlom, Molecular Foundations of Oncology, pp. 95–134, 1991.*

Fitzpatrick et al., "Formation of a high affinity heregulin binding site using the soluble extracellular domains of ErbB2 with ErbB3 or ErbB4" *FEBS Letters* 431(1):102–106 (Jul. 10, 1998).

Ahmed., "A New Rapid and Simple Non–Radioactive Assay to Monitor and Determine the Proliferation of Lymphocytes: An Alternative to [3H] Thymidine Incorporation Assay." *J. Immunol. Methods* 170:211–224 (1994).

Baca et al., "Antibody Humanization Using Monovalent Phage Display" *Journal of Biological Chemistry* 272(16):10678–10684 (1997).

Bos, Johannes L., "A Target for Phosphoinositide 3–Kinase: Akt/PKB" *Trends Biochem. Sci.* 20:441–442 (Nov. 1995).

Carraway et al., "Heregulin Stimulates Mitogenesis and Phosphatidylinositol 3–Kinase in Mouse Fibroblasts Transfected with erbB2/neu and erbB3" *J. Bio. Chem.* 270:7111–7116 (Mar. 1995).

Krymskaya et al., "EGF Activates ErbB–2 and Stimulates Phosphatidylinositol 3–Kinase in Human Airway Smooth Muscle Cells." *Am. J. Physiol.* 276:L246–L255 (1999).

Olayioye et al., "ErbB–1 and ErbB–2 Acquire Distinct Signaling Properties Dependent Upon Their Dimerization Partner." *Molecular & Cellular Biology* 18:5042–5051 (Sep. 1998).

Page et al., "A New Fluorometric Assay for Cytotoxicity Measurements In Vitro." *Int. J. Oncol.* 3:473–476 (1993).

Sugarman et al., "Recombinant Human Tumor Necrosis Factor–α: Effects on Proliferation of Normal and Transformed Cells in Vitro" *Science* 230:943–945 (1985).

Tan et al., "Heregulin β1–Activated Phosphatidylinositol 3–Kinase Enhances Aggregation of MCF–7 Breast Cancer Cells Independent of Extracellular Signal–Regulated Kinase." *Cancer Research.* 59:1620–1625 (Apr. 1999).

Aasland et al., "Expression of oncogenes in thyroid tumours: Coexpression of c–erbB2/neu and c–erbB" *British Journal of Cancer* 57(4):358–363 (Apr. 1988).

Akiyama et al., "Tumor Promoter and Epidermal Growth Factor Stimulate Phosphorylation of the c–erbB–2 Gene Product in MKN–7 Human Adenocarcinoma Cells" *Molecular & Cellular Biology* 8(3):1019–1026 (Mar. 1988).

Arteaga et al., "$p185^{c-erbB-2}$ Signaling Enhances Cisplatin–induced Cytotoxicity in Human Breast Carcinoma Cells: Association Between an Oncogenic Receptor Tyrosine Kinase and Drug–induced DNA Repair" *Cancer Research* 54(14):3758–3765 (Jul. 15, 1994).

Bacus et al., "Differentiation of Cultured Human Breast Cancer Cells (AU–565 and MCF–7) Associated With Loss of Cell Surface HER–2/neu Antigen" *Molecular Carcinogenesis* 3(6):350–362 (1990).

Bacus et al., "Tumor–inhibitory Monoclonal Antibodies to the HER–2/Neu Receptor Induce Differentiation of Human Breast Cancer Cells" *Cancer Research* 52(9):2580–2589 (May 1, 1992).

Baselga et al., "Phase II Study of Weekly Intravenous Recombinant Humanized Anti–$p185^{HER2}$ Monoclonal Antibody in Patients With HER2/neu–Overexpressing Metastatic Breast Cancer" *J. Clin. Oncol.* 14(3):737–744 (Mar. 1996).

Baselga et al., "Receptor Blockade With Monoclonal Antibodies As Anti–Cancer Therapy" *Pharmac. Ther.* 64:127–154 (1994).

Borst et al., "Oncogene Alterations in Endometrial Carcinoma" *Gynecologic Oncology* 38(3):364–366 (Sep. 1990).

Burden et al., "Neuregulins and their receptors: a versatile signaling module in organogenesis and oncogenesis" *Neuron* 18(6):847–855 (Jun. 1997).

Carraway et al., "A Neu Acquaintance for ErbB3 and ErbB4: A Role for Receptor Heterodimerization in Growth Signaling" *Cell* 78:5–8 (Jul. 15, 1994).

Carraway et al., "Neuregulin–2, a new ligand of ErbB3/ErbB4–receptor tyrosine kinases" *Nature* 387:512–516 (May 1997).

Carter et al., "Humanization of an anti–$p185^{HER2}$ antibody for human cancer therapy" *Proc. Natl. Acad. Sci.* 89:4285–4289 (May 1992).

Chang et al., "Ligands for ErbB–family receptors encoded by a neuregulin–like gene" *Nature* 387:509–512 (May 29, 1997).

Cohen et al., "Expression pattern of the neu (NGL) gene–encoded growth factor receptor protein ($p185^{neu}$) in normal and transformed epithelial tissues of the digestive tract" *Oncogene* 4(1):81–88 (Jan. 1989).

Connelly et al., "The epidermal growth factor receptor and the product of the neu protooncogene are members of a receptor tyrosine phosphorylation cascade" *Proc. Natl. Acad. Sci. USA* 87:6054–6057 (Aug. 1990).

Craft et al., "A mechanism for hormone–independent prostate cancer through modulation of androgen receptor signaling by the HER–2/neu tyrosine kinase" *Nature Medicine* 5(3):280–285 (Mar. 1999).

D'souza et al., "Overexpression of ERBB2 in human mammary epithelial cells signals inhibition of transcription of the E–cadherin gene" *Proc. Natl. Acad. Sci. USA* 91(15):7202–7206 (Jul. 19, 1994).

Drebin et al., "Down–Modulation of an Oncogene Protein Product and Reversion of the Transformed Phenotype by Monoclonal Antibodies" *Cell* 41(3):695–706 (Jul. 1985).

Drebin et al., "Monoclonal antibodies reactive with distinct domains of the neu oncogene–encoded p185 molecule exert synergistic anti–tumor effects in vivo" *Oncogene* 2:273–277 (1988).

Earp et al., "Heterodimerization and functional interaction between EGF receptor family members: A new signaling paradigm with implications for breast cancer research" *Breast Cancer Res and Treatment* 35:115–132 (1995).

Fendly et al., "Characterization of Murine Monoclonal Antibodies Reactive to Either the Human Epidermal Growth Factor Receptor of HER2/neu Gene Product" *Cancer Research* 50:1550–1558 (Mar. 1, 1990).

Fukushige et al., "Localization of a novel v–erbB–related gene, c–erbB–2, on human chromosome 17 and its amplification in a gastric cancer cell line" *Molecular & Cellular Biology* 6(3):955–958 (Mar. 1986).

Goldman et al., "Heterodimerization of the erbB–1 and erbB–2 Receptors in Human Breast Carcinoma Cells: A Mechanism for Receptor Transregulation" *Biochemistry* 29(50):11024–11028 (1990).

Graus–Porta et al., "ErbB–2, the preferred heterodimerization partner of all ErbB receptors, is a mediator of lateral signaling" *EMBO Journal* 16(7):1647–1655 (1997).

Groenen et al., "Structure–Function Relationships for the EGF/TGF–α Family of Mitogens" *Growth Factors* 11:235–257 (1994).

Gu et al., "Overexpression of her–2/neu in human prostate cancer and benign hyperplasia" *Cancer Lett.* 99:185–189 (1996).

Guerin et al., "Overexpression of Either c–myc or c–erbB–2/neu Proto–Oncogenes in Human Breast Carcinomas: Correlation with Poor Prognosis" *Oncogene Res* 3:21–31 (1988).

Hancock et al., "A Monoclonal Antibody against the c–erbB–2 Protein Enhances the Cytotoxicity of cis–Diamminedichloroplatinum against Human Breast and Ovarian Tumor Cell Lines" *Cancer Research* 51:4575–4580 (Sep. 1, 1991).

Harari et al., "Neuregulin–4: a novel growth factor that acts through the ErbB–4 receptor tyrosine kinase" *Oncogene* 18:2681–2689 (1999).

Harwerth et al., "Monoclonal Antibodies against the Extracellular Domain of the erbB–2 Receptor Function as Partial Ligand Agonists" *Journal of Biological Chemistry* 267(21):15160–15167 (Jul. 25, 1992).

Holmes et al., "Identification of Heregulin, a Specific Activator of p185$^{erbB2}$" *Science* 256:1205–1210 (May 22, 1992).

Hudziak et al., "Increased expression of the putative growth factor receptor p185$^{her2}$ causes transformation and tumorigenesis of NIH 3T3 cells" *Proc. Natl. Acad. Sci.* 84(20):7159–7163 (Oct. 1987).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (Mar. 1989).

Jones et al., "Binding Interaction of the Heregulinβ egf Domain with ErbB3 and ErbB4 Receptors Assessed by Alanine Scanning Mutagenesis" *Journal of Biological Chemistry* 273(19):11667–11674 (May 8, 1998).

Kannan et al., "Cripto Enhances the Tyrosine Phosphorylation of Shc and Activates Mitogen–activated Protein Kinase (MAPK) in Mammary Epithelial Cells" *Journal of Biological Chemistry* 272(6):3330–3335 (Feb. 7, 1997).

Karunagaran et al., "ErbB–2 is a Common Auxiliary Subunit of NDF and EGF Receptors: Implications for Breast Cancer" *EMBO Journal* 15(2):254–264 (1996).

Kasprzyk et al., "Therapy of an Animal Model of Human Gastric Cancer Using a Combination of Anti–erbB–2 Monoclonal Antibodies" *Cancer Research* 52(10):2771–2776 (May 15, 1992).

Kern et al., "p185$^{neu}$ Expression in Human Lung Adenocarcinomas Predicts Shortened Survival" *Cancer Research* 50(16):5184–5191 (Aug. 15, 1990).

King et al., "Amplification of a Novel v–erbB–Related Gene in a Human Mammary Carcinoma" *Science* 229:974–976 (Sep. 1985).

King et al., "EGF binding to its receptor triggers a rapid tyrosine phosphorylation of the erbB–2 protein in the mammary tumor cell line SK–BR–3" *EMBO Journal* 7(6):1647–1651 (1988).

Klapper et al., "A subclass of tumor–inhibitory monoclonal antibodies to ErbB–2/HER2 blocks crosstalk with growth factor receptors" *Oncogene* 14:2099–2109 (1997).

Kokai et al., "Synergistic Interaction of p185c–neu and the EGF Receptor Leads to Transformation of Rodent Fibroblasts" *Cell* 58:287–292 (Jul. 28, 1989).

Kotts et al., "Differential Growth Inhibition of Human Carcinoma Cells Exposed to Monoclonal Antibodies Directed against the Extracellular Domain of the HER2/ERBB2 Protooncogene" *In Vitro* (Abstract #176) 26(3):59A (1990).

Kotts et al., "Growth Inhibition of Human Breast Carcinoma Cells Exposed to Combinations of Interferon–Gamma and Monoclonal Antibodies Directed Against the Extracellular Domain of the Her2/erbB2 Oncogene Protein" *FASEB Journal* (abstract #1470) 4(7):A1946 (1990).

Kotts et al., "Growth Inhibition of Human Breast Carcinoma Cells Exposed to Combinations of Interferon–gamma and Monoclonal Antibodies Directed against the Extracellular Domain of the HER2/ERBB2 Protooncogene" (Program 1470, Joint Mtg of ASBMB & AAI in New Orleans, LA on Jun. 4–7, 1990 poster).

Kraus et al., "Isolation and characterization of ERBB3, a third member of the ERBB/epidermal growth factor receptor family: Evidence for overexpression in a subset of human mammary tumors" *Proc. Natl. Acad. Sci. USA* 86:9193–9197 (Dec. 1989).

Kumar et al., "Regulation of Phosphorylation of the c–erbB–2/HER2 Gene Product by a Monoclonal Antibody and Serum Growth Factor(s) in Human Mammary Carcinoma Cells" *Molecular & Cellular Biology* 11(2):979–986 (Feb. 1991).

Lee et al., "Transforming Growth Factor α: Expression, Regulation, and Biological Activities" *Pharmacological Reviews* 47(1):51–85 (Mar. 1995).

Lemke, G., "Neuregulins in Development" *Molecular and Cellular Neuroscience* 7:247–262 (1996).

Levi et al., "The Influence of Heregulins on Human Schwann Cell Proliferation" *J. Neuroscience* 15(2):1329–1340 (Feb. 1995).

Lewis et al., "Differential responses of human tumor cell lines to anti–p185$^{HER2}$ monoclonal antibodies" *Cancer Immunol. Immunother.* 37:255–263 (1993).

Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457–1465 (Mar. 15, 1996).

Maier et al., "Requirements for the Internalization of a Murine Monoclonal Antibody Directed against the HER–2/neu Gene Product c–erbB–2" *Cancer Research* 51(19):5361–5369 (Oct. 1, 1991).

Masui et al., "Growth Inhibition of Human Tumor Cells in Athymic Mice by Anti–Epidermal Growth Factor Receptor Monoclonal Antibodies" *Cancer Research* 44(3):1002–1007 (Mar. 1984).

McCann et al., "c–erbB–2 Oncoprotein Expression in Primary Human Tumors" *Cancer* 65(1):88–92 (Jan. 1, 1990).

McKenzie et al., "Generation and characterization of monoclonal antibodies specific for the human neu oncogene product, p185" *Oncogene* 4:543–548 (1989).

"Could Medarex's MAb be prostate cancer's Herceptin?" *Scrip* 2442:25 (Jun. 2, 1999).

Morrissey et al., "Axon–induced mitogenesis of human Schwann cells involves heregulin and p185$^{erbB2}$" *Proc. Natl. Acad. Sci. USA* 92:1431–1435 (Feb. 1995).

Myers et al., "Biological Effects of Monoclonal Antireceptor Antibodies Reactive with neu Oncogene Product, p185$^{neu}$" *Methods in Enzymology* 198:277–290 (1991).

Park et al., "Amplification, Overexpression, and Rearrangement of the erbB–2 Protooncogene in Primary Human Stomach Carcinomas" *Cancer Research* 49(23):6605–6609 (Dec. 1, 1989).

Pietras et al., "Antibody to HER–2/neu receptor blocks DNA repair after cisplatin in human breast and ovarian cancer cells" *Oncogene* 9:1829–1838 (1994).

Plowman et al., "Heregulin induces tyrosine phosphorylation of HER4/p180$^{erbB4}$" *Nature* (Letters to Nature) 366:473–475 (Dec. 2, 1993).

Plowman et al., "Ligand–specific activation of HER4/p180$^{erbB4}$, a fourth member of the epidermal growth factor receptor family" *Proc. Natl. Acad. Sci. USA* 90:1746–1750 (Mar. 1993).

Presta et al., "Humanization of an Anti–Vascular Endothelial Growth Factor Monoclonal Antibody for the Therapy of Solid Tumors and Other Disorders" *Cancer Research* 57(20):4593–4599 (Oct. 15, 1997).

Ross et al., "HER–2/neu Gene Amplification Status in Prostate Cancer by Fluorescence in Situ Hybridization" *Hum. Pathol.* 28(7):827–833 (Jul. 1997).

Ross et al., "Prognostic Significance of HER–2/neu Gene Amplification Status by Fluorescence In Situ Hybridization of Prostate Carcinoma" *Cancer* 79(11):2162–2170 (Jun. 1, 1997).

Sadasivan et al., "Overexpression of Her–2/Neu May Be An Indicator of Poor Prognosis in Prostate Cancer" *J. Urol.* 150:126–131 (Jul. 1993).

Sarup et al., "Characterization of an Anti–P185$^{HER2}$ Monoclonal Antibody that Stimulate Receptor Function and Inhibits Tumor Cell Growth" *Growth Regulation* 1:72–82 (1991).

Schaefer et al., "A Discrete Three–amino Acid Segment (LVI) at the C–terminal End of Kinase–impaired ErbB3 is required for Transactivation of ErbB2" *Journal of Biological Chemistry* 274(2):859–866 (Jan. 8, 1999).

Schaefer et al., "γ–Heregulin: a novel heregulin isoform that is an autocrine growth factor for the human breast cancer cell line, MDA–MB–175" *Oncogene* 15:1385–1394 (1997).

Scher et al., "Changing Pattern of Expression of the Epidermal Growth Factor Receptor and Transforming Growth Factor α in the Progression of Prostatic Neoplasms" *Clinical Cancer Research* 1:545–550 (May 1995).

Scott et al., "p185$^{HER2}$ Signal Transduction in Breast Cancer Cells" *Journal of Biological Chemistry* 266(22):14300–14305 (Aug. 5, 1991).

Shawver et al., "Ligand–like Effects Induced by Anti–c–erbB–2 Antibodies Do Not Correlate with and Are Not Required for Growth Inhibition of Human Carcinoma Cells" *Cancer Research* 54(5):1367–1373 (Mar. 1, 1994).

Sheng et al., "Inhibition of Human Colon Cancer Cell Growth by Selective Inhibition of Cyclooxygenase–2" *J. Clin. Invest.* 99(9):2254–2259 (May 1997).

Shepard et al., "Monoclonal Antibody Therapy of Human Cancer: Taking the HER2 Protooncogene to the Clinic" *J. Clin. Immunol.* 11(3):117–127 (1991).

Slamon et al., "Human Breast Cancer: Correlation of Relapse and Survival with Amplification of the HER–2/neu Oncogene" *Science* 235:177–182 (Jan. 9, 1987)

Slamon et al., "Studies of the HER–2/neu Proto–oncogene in Human Breast and Ovarian Cancer" *Science* 244:707–712 (May 12, 1989).

Sliwkowski et al., "Coexpression of erbB2 and erbB3 Proteins Reconstitutes a High Affinity Receptor for Heregulin" *Journal of Biological Chemistry* 269(20):14661–14665 (May 20, 1994).

Stancovski et al., "Mechanistic aspects of the opposing effects of monoclonal antibodies to the ERBB2 receptor on tumor growth" *Proc. Natl. Acad. Sci. USA* 88(19):8691–8695 (Oct. 1, 1991).

Stern et al., "EGF–stimulated Tyrosine Phosphorylation of p185$^{neu}$: a potential model for receptor interactions" *EMBO Journal* 7(4):995–1001 (1988).

Tagliabue et al., "Selection of monoclonal antibodies which induce internalization and phosphorylation of p185$^{HER2}$ and growth inhibition of cells with HER2/NEU gene amplification" *International Journal of Cancer* 47(6):933–937 (Apr. 1, 1991).

Vadlamudi et al., "Regulation of Cyclooxygenase–2 pathway by HER2 receptor" *Oncogene* 18:305–314 (1999).

Vitetta et al., "Monoclonal Antibodies as Agonists: An Expanded Role for Their Use in Cancer Therapy" *Cancer Research* 54(20):5301–5309 (Oct. 15, 1994).

Wada et al., "Intermolecular Association of the p185$^{neu}$ Protein and EGF Receptor Modulates EGF Receptor Function" *Cell* 61:1339–1347 (Jun. 29, 1990).

Weiner et al., "Expression of the neu Gene–encoded Protein (P185$^{neu}$) in Human Non–Small Cell Carcinomas of the Lung" *Cancer Research* 50(2):421–425 (Jan. 15, 1990).

Werther et al., "Humanization of an Anti–Lymphocyte Function–Associated Antigen (LFA)–1 Monoclonal Antibody and Reengineering of the Humanized Antibody for Binding to Rhesus LFA–1" *J. of Immunology* 157:4986–4995 (1996).

Williams et al., "Expression of c–erbB–2 in Human Pancreatic Adenocarcinomas" *Pathobiology* 59(1):46–52 (1991).

Wofsy et al., "Modification and Use of Antibodies to Label Cell Surface Antigens" *Selected Methods in Cellular Immunology*, Mishel and Schiigi, eds., San Francisco:WJ Freeman Co., Chapter 13, pp. 287–304 (1980).

Worthylake et al., "Structural Aspects of the Epidermal Growth Factor Receptor Required for Transmodulation of erbB–2/neu" *Journal of Biological Chemistry* 272(13):8594–8601 (Mar. 28, 1997).

Wright et al., "An Incomplete Program of Cellular Tyrosine Phosphorylations Induced by Kinase–defective Epidermal Growth Factor Receptors" *Journal of Biological Chemistry* 270(20):12085–12093 (May 19, 1995).

Wu et al., "Apoptosis Induced By an Anti–Epidermal Growth Factor Receptor Monoclonal Antibody in a Human Colorectal Carcinoma Cell Line and Its Delay By Insulin" *Journal of Clinical Investigation* 95(4):1897–1905 (Apr. 1995).

Xu et al., "Antibody–induced growth inhibition is mediated through immunochemically and functionally distinct epitopes on the extracellular domain of the c–erbB–2 (HER–2/neu) gene product p185" *International Journal of Cancer* 53(3):401–408 (Feb. 1, 1993).

Yeh et al., "From HER2/Neu signal cascade to androgen receptor and its coactivators: A novel pathway by induction of androgen target genes through MAP kinase in prostate cancer cells" *Proc. Natl. Acad. Sci. USA* 96:5458–5463 (May 1999).

Yokota et al., "Amplification of c–erbB–2 Oncogene in Human Adenocarcinomas in Vivo" *Lancet* 1(8484):765–767 (Apr. 5, 1986).

Yonemura et al., "Evaluation of Immunoreactivity for erbB–2 Protein as a Marker of Poor Short Term Prognosis in Gastric Cancer" *Cancer Research* 51(3):1034–1038 (Feb. 1, 1991).

Zhang et al., "Neuregulin–3 (NRG3): A novel neural tissue–enriched protein that binds and activates ErbB4" *Proc. Natl. Acad. Sci. USA* 94:9562–9567 (Sep. 22, 1997).

Zhau et al., "Amplification and Expression of the c–erb B–2/neu Proto–Oncogene in Human Bladder Cancer" *Molecular Carcinogenesis* 3(5):254–257 (1990).

Agus at al., "Differential Anti–Tumor Effects of Targeting Distinct Epitopes of the Her–2/neu Extracellular Domain in Xenograft Models of Prostate Cancer." *Proceedings of the American Association for Cancer Research Annual Meeting* (Abstract #4570) 41:719 (Mar. 2000).

Agus et al., "Response of Prostate Cancer to Anti–Her–2/neu Antibody in Androgen–Dependent and –Independent Human Xenograft Models" *Cancer Research* 59:4761–4764 (1999).

*American Cancer Society Textbook of Clinical Oncology*, Murphy et al., 2nd edition, Atlanta:American Cancer Society pp. 126–127 (1995).

Ching, K., "Role of c–erb B gene family in prostate cancer" *Dissertation Abstracts International* 55(11):4738–B (May 1995).

Curnow, R., "Clinical experience with CD64–directed immunotherapy. An overview" *Cancer Immunology and Immunotherapy* 45(3–4):210–215 (Nov.–Dec. 1997).

Curti, B., "Physical barriers to drug delivey in tumors" *Critical Reviews in Oncology–Hematology* 14(1):29–39 (Feb. 1993).

Ezeh et al., "Differential activation of ErbB receptors in the rat olfactory mucosa by transforming growth factor–α and epidermal growth factor in vivo" *Journal of Neurobiology* 37(2):199–210 (Nov. 5, 1998).

Gibson et al., "A novel method for real time quantitative RT–PCR" *Genome Research* 6(10):995–1001 (Oct. 1996).

Gura, T., "Systems for identifying new drugs are often faulty" *Science* 278(5340):1041–1042 (Nov. 7, 1997).

Heid et al., "Real time quantitative PCR" *Genome Research* 6(10):986–994 (1996).

Jain, R., "Barriers to drug delivery in solid tumors" *Scientific American* 271(1):58–65 (Jul. 1994).

James et al., "Phae II Trial of the Bispecific Antibody MDX–H210 (anti–Her2/Neu X anti–CD64) Combined With GM–CSF in Patients With Advanced Prostate and Renal Cell Carcinoma That Express Her2/Neu." *British Journal of Cancer* (Abstract #56) 78:19 (1998).

James et al., "Phase II trial of the bispecific antibody MDX–H210 (anti–HER2/NEU X anti–CD64) combined with GM–CSF in patients with advanced prostate and renal cell carcinomas that express HER2/NEU" *Proc. Annu. Meet. Soc. Clin. Oncol.* (Abstract No. 1681) 17:436a (1998).

Kabat. *Sequences of Proteins of Immunological Interest*, US Dept of Health and Human Services, NIH, 5th edition, Bethesda, MD (1991).

Knox et al., "Yttrium–90–labeled anti–CD20 monoclonal antibody therapy of recurrent B–cell lymphoma" *Clinical Cancer Research* 2(3):457–470 (Mar. 1996).

Medarex, Inc., "Medarex's HER–2 product show anti–cancer effects in phase II prostate and kidney studies" (company press release) (May 19, 1998).

Myers et al., "Intracellular antibody mediated down–regulation of p185$^{erbB-2}$ expression in malignant prostatic cells" *Proceedings of the American Association for Cancer Research Annual Meeting* (Abstract #2334) 37:342 (1996).

Nagabhushan et al., "CWR22: The First Human Prostate Cancer Xenograft with Strongly Androgen–dependent and Relapsed Strains Both in Vivo and in Soft Agar" *Cancer Research* 56:3042–3046 (1996).

Nagy et al., "Complexity of signal transduction mediated by ErbB2: clues to the potential of receptor–targeted cancer therapy" *Pathology Oncology Research* 5(4):255–271 (1999).

Okabayashi et al., "Podofilox–induced regression of Shope papillomas may be indpendent of host immunity" *Journal of Investigative Dermatology* 101(6):852–857 (Dec. 1993).

Okuda et al., "The cytostome of Trypanosoma cruzi epimastigotes is associated with the flagellar complex" *Experimental Parasitology* 92(4):223–231 (Aug. 1999).

Sato et al., "A Metastatic and Androgen–sensitive Human Prostate Cancer Model Using Intraprostatic Inoculation of LNCaP Cells in SCID Mice" *Cancer Research* 57:1584–1589 (1997).

Skrepnik et al., "Recombinant Oncotoxin AR209 (anti–p185$^{erbB-2}$) Diminishes Human Prostate Carcinoma Xenografts" *Journal of Urology* 161:984–989 (1999).

Stearns et al., "Workgroup 2: Human Xenograft Models of Prostate Cancer" *Prostate* 36:56–58 (1998).

Wainstein et al., "CWR22: Androgen–dependent Xenograft Model Derived from a Primary Human Prostatic Carcinoma" *Cancer Research* 54:6049–6052 (1994).

Baselga et al., "Anti HER2 Humanized Monoclonal Antibody (MAb) Alone and in Combination with Chemotherapy Against Human Breast Carcinoma Xenografts" *Proceedings of ASCO—13th Annual Meeting* (Abstract #53), Dallas, TX 13:63 (Mar. 1994).

Baselga et al., "HER2 overexpression and paclitaxel sensitivity in breast cancer: therapeutic implications" *Oncology* 11(3 Suppl 2):43–48 (Mar. 1997).

Baselga et al., "Monoclonal antibodies directed againt growth factor receptors enhance the efficacy of chemotherapeutic agents" *Annals of Oncology* (abstract #010) 5(Suppl. 5) (1994).

Baselga et al., "Recombinant Humanized Anti–HER2 Antibody (Herceptin) Enhances the Antitumor Activity of Paclitaxel and Doxorubicin against HER2/neu Overexpressing Human Breast Cancer Xenografts" *Cancer Research* 58:2825–2831 (Jul. 1998).

De Santes et al., "Radiolabeled Antibody Targeting of the HER–2/neu Oncoprotein" *Cancer Research* 52:1916–1923 (1992).

DiFiore et al., "erbB–2 is a potent oncogene when overexpressed in NIH/3T3 cells" *Science* 237(4811):178–182 (Jul. 10, 1987).

Drebin et al., "Inhibition of tumor growth by a monoclonal antibody reactive with an oncogene–encoded tumor antigen" *Proc. Natl. Acad. Sci.* 83:9129–9133 (1986).

Drebin et al., "Monoclonal Antibodies Specific for the neu Oncogene Product Directly Mediate Anti–tumor Effects In Vivo" *Oncogene* 2(4):387–394 (1988).

Fleiss, JL *Statistical Methods for Rates and Proportions*, 2nd edition, New York, NY:Wiley pp. 13–17 (1981).

Gemzar (gemcitabine HCL), "Product Information—PDR" (2000).

Green et al., "Preclinical Evaluation of WR–151327: An Orally Active Chemotherapy Protector" *Cancer Research* 54(3):738–741 (Feb. 1, 1994).

Guy et al., "Expression of the neu protooncogene in the mammary epithelium of transgenic mice induces metastatic disease" *Proc. Natl. Acad. Sci. USA* 89(22):10578–10582 (Nov. 15, 1992).

Hynes and Stern, "The biology of erbB–2/neu/HER–2 and its role in cancer" *Biochimica et Biophysica Acta* 1198(2–3):165–184 (Dec. 30, 1994).

Ilgen et al., "Characterization of anti–HER/2 antibodies which inhibit the growth of breast tumor cells in vitro" *Proceedings of the American Association for Cancer Research* (abstract #3209) 37:470 (Mar. 1996.

Masuko et al., "A murine Monoclonal Antibody That Recognizes an Extracellular Domain of the Human c–erbB–2 Protooncogene Product" *Jpn J. Cancer Res.* 80:10–14 (Jan. 1989).

Mendelsohn et al., "Receptor blockade and chemotherapy: a new approach to combination cancer therapy" *Annals of Oncology* (abstract #040) 7(Suppl. 1):22 (1996).

Norton, L, "Evolving concepts in the systemic drug therapy of breast cancer" *Seminars in Oncology* 24(4 Suppl 10):S10–3–S10–10 (Aug. 1997).

Pegram et al., "Inhibitory effects of combinations of HER–2/neu antibody and chemotherapeutic agents used for treatment of human breast cancers" *Oncogene* 18:2241–2251 (1999).

Raefsky et al., "Phase II Trial of Docetaxel and Herceptin as First– or Second–Line Chemotherapy for Women with Metastatic Breast Cancer Whose Tumors Overexpress HER2" *Proceedings of ASCO* (*Abstract #523*) 18:137a (1999).

Ravdin and Chamness, "The c–erbB–2 proto–oncogene as a prognostic and predictive marker in breast cancer: a paradigm for the development of other macromolecular markers—a review" *Gene* 159(1):19–27 (Jun. 14, 1995).

Rodeck et al., "Interactions between growth factor receptors and corresponding monoclonal antibodies in human tumors" *J. Cellular Biochem.* 35(4):315–320 (1987).

Schlom, J., "Monoclonal Antibodies: They're More and Less Than You Think" *Molecular Foundations of Oncology*, Broder, S. ed., Baltimore, MD:Williams & Wilkins, Chapter 6, pp. 95–134 (1991).

Seifert et al., "Dexrazoxane in the prevention of doxorubicin–induced cardiotoxicity" *Annals of Pharmacotherapy* 28(9):1063–1072 (Sep. 1994).

Singal and Iliskovic, "Doxorubicin–induced cardiomyopathy" *New England J. of Medicine* 339(13):900–905 (Sep. 24, 1998).

Singal et al., "Combination therapy with probucol prevents adriamycin–induced cardiomyopathy" *Journal of Molecular & Cellular Cardiology* 27(4):1055–1063 (Apr. 1995).

Sliwkowski et al., "A humanized monoclonal antibody for the treatment of HER2 overexpressing breast cancer" *Proceedings of the American Association for Cancer Research* 37:625–626 (Mar. 1996).

Zhang et al., "Shared antigenic epitopes and pathobiological functions of anti–p185$^{ner2/neu}$ monoclonal antibodies" *Experimental and Molecular Pathology* 67:15–25 (1999).

* cited by examiner

```
  1 MELAALCRWG LLLALLPPGA ASTQVCTGTD MKLRLPASPE THLDMLRHLY QGCQVVQGNL ELTYLPTNAS LSFLQDIQEV VRQVPLQRLR
101 IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK
201 GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP
301 YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF
401 ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP
501 EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC
601 PSGVKPDLSY MPIWKFPDEE GACQPCPINC THSCVDLDDK GCPAE (SEQ ID NO:13)
```

Fig. 1A

7C2   aa  22-53    (31 residues)

7F3   aa  22-53    (31 residues)

2C4   aa  22-584   (562 residues)

7D3   aa  22-584   (562 residues)

3E8   aa 512-625   (113 residues)

4D5   aa 529-625   (96 residues)

2H11  aa 529-645   (116 residues)

3H4   aa 541-599   (58 residues)

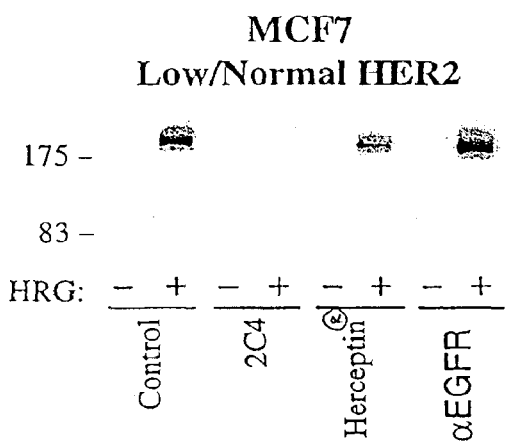
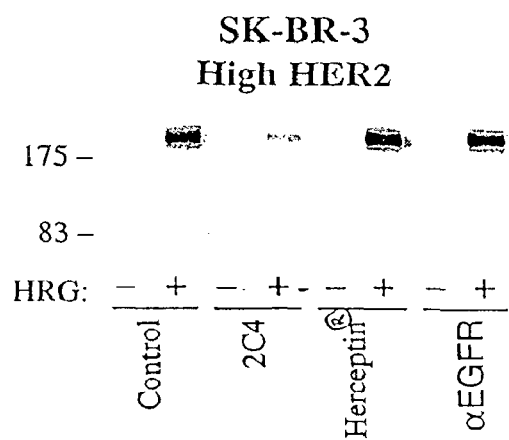
Fig. 5A  MCF7 Low/Normal HER2
Fig. 5B  SK-BR-3 High HER2
IP: αHER2
WB: αHER3

Fig. 7A: Variable Light

```
                  10         20         30          40
2C4       DTVMTQSHKIMSTSVGDRVSITC [KASQDVSIGVA] WYQQRP
           **     ****  *          *                *
574       DIQMTQSPSSLSASVGDRVTITC [KASQDVSIGVA] WYQQKP
                                      *     * hum κI    DIQMTQSPSSLSASVGDRVTITC [RASQSISNYLA] WYQQKP 50         60         70          80
2C4       GQSPKLLIY [SASYRYT] GVPDRFTGSGSGTDFTFTISSVQA
           **                      *  *        *   * *
574       GKAPKLLIY [SASYRYT] GVPSRFSGSGSGTDFTLTISSLQP
                    * ***** hum κI    GKAPKLLIY [AASSLES] GVPSRFSGSGSGTDFTLTISSLQP 90        100
2C4       EDLAVYYC [QQYYIYPYT] FGGGTKLEIK    (SEQ ID NO:1)
           * *                   *  *
574       EDFATYYC [QQYYIYPYT] FGQGTKVEIK    (SEQ ID NO:3)
                   *** * hum κI    EDFATYYC [QQYNSLPWT] FGQGTKVEIK    (SEQ ID NO:5)
```

Fig. 7B: Variable Heavy

```
                  10         20         30          40
2C4       EVQLQQSGPELVKPGTSVKISCKAS [GFTFTDYTMD] WVKQS
           **    **   *   *  ***  *                *  *
574       EVQLVESGGGLVQPGGSLRLSCAAS [GFTFTDYTMD] WVRQA
                                     ** *  * hum III   EVQLVESGGGLVQPGGSLRLSCAAS [GFTFSSYAMS] WVRQA 50     a      60            70          80
2C4       HGKSLEWIG [DVNPNSGGSIYNQRFKG] KASLTVDRSSRIVYM
           *  *    **                    *** *    **** *
574       PGKGLEWVA [DVNPNSGGSIYNQRFKG] RFTLSVDRSKNTLYL
                    ****  * ****      *  * hum III   PGKGLEWVA [VISGDGGSTYYADSVKG] RFTISRDNSKNTLYL abc      90        100ab         110
2C4       ELRSLTFEDTAVYYCAR [NLGPSFYFDY] WGQGTTLTVSS (SEQ ID NO:2)
           ***  **                                **
574       QMNSLRAEDTAVYYCAR [NLGPSFYFDY] WGQGTLVTVSS (SEQ ID NO:4)
                                ******** hum III   QMNSLRAEDTAVYYCAR [GRVGYSLYDY] WGQGTLVTVSS (SEQ ID NO:6)
```

HUMANIZED ANTI-ERBB2 ANTIBODIES AND TREATMENT WITH ANTI-ERBB2 ANTIBODIES

RELATED APPLICATIONS

This application is a non-provisional application filed under 37 CFR 1.53(b)(1), claiming priority under 35 USC 119(e) to provisional application No. 60\141,316 filed Jun. 25, 1999, the contents of which are incorporated herein by reference.

FIELD OF THE INVENTION

The present invention concerns humanized anti-ErbB2 antibodies and methods for treating cancer with anti-ErbB2 antibodies, such as humanized anti-ErbB2 antibodies.

BACKGROUND OF THE INVENTION

The ErbB family of receptor tyrosine kinases are important mediators of cell growth, differentiation and survival. The receptor family includes four distinct members including epidermal growth factor receptor (EGFR or ErbB1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatury pathway. Baselga and Mendelsohn *Pharmac. Ther.* 64:127–154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research.* 44:1002–1007 (1984); and Wu et al. *J. Clin. Invest.* 95:1897–1905 (1995).

The second member of the ErbB family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177–182 (1987); Slamon et al., *Science,* 244:707–712 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765–767 (1986); Fukushige et al., *Mol Cell Biol.,* 6:955–958 (1986); Guerin et al., *Oncogene Res.,* 3:21–31 (1988); Cohen et al., *Oncogene,* 4:81–88 (1989); Yonemura et al., *Cancer Res.,* 51:1034 (1991); Borst et al., *Gynecol. Oncol.,* 38:364 (1990); Weiner et al., *Cancer Res.,* 50:421–425 (1990); Kern et al., *Cancer Res.,* 50:5184 (1990); Park et al., *Cancer Res.,* 49:6605 (1989); Zhau et al., *Mol. Carcinog.,* 3:254–257 (1990); Aasland et al. *Br. J. Cancer* 57:358–363 (1988); Williams et al. *Pathobiology* 59:46–52 (1991); and McCann et al., *Cancer,* 65:88–92 (1990). ErbB2 may be overexpressed in prostate cancer (Gu et al. *Cancer Lett.* 99:185–9 (1996); Ross et al. *Hum. Pathol.* 28:827–33 (1997); Ross et al. *Cancer* 79:2162–70 (1997); and Sadasivan et al. *J. Urol.* 150:126–31 (1993)).

Antibodies directed against the rat p185$^{neu}$ and human ErbB2 protein produces have been described. Drebin and colleagues have raised antibodies against the rat neu gene product, p185$^{neu}$ See, for example, Drebin et al., *Cell* 41:695–706 (1985); Myers et al., *Meth. Enzym.* 198:277–290 (1991); and WO94/22478. Drebin et al. *Oncogene* 2:273–277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165–1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al are further characterized in Fendly et al *Cancer Research* 50:1550–1558 (1990); Kotts et al. In Vitro 26(3):59A (1990); Sarup et al. *Growth Regulation* 1:72–82 (1991); Shepard et al *J. Clin. Immunol.* 11(3):117–127 (1991); Kumar et al. *Mol. Cell. Biol.* 11(2):979–986 (1991); Lewis et al *Cancer Immunol. Immunother.* 37:255–263 (1993); Pietras et al *Oncogene* 9:1829–1838 (1994); Vitetta et al *Cancer Research* 54:5301–5309 (1994); Sliwkowski et al. *J. Biol. Chem.* 269(20):14661–14665 (1994); Scott et al. *J. Biol. Chem.* 266:14300–5 (1991); D'souza et al *Proc. Natl. Acad. Sci.* 91:7202–7206 (1994); Lewis et al. *Cancer Research* 56:1457–1465 (1996); and Schaefer et al. *Oncogene* 15:1385–1394 (1997).

A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anticancer therapy (Baselga et al., *J. Clin. Oncol.* 14:737–744 (1996)). HERCEPTIN® received marketing approval from the Food and Drug Administration Sep. 25, 1998 for the treatment of patients with metastatic breast cancer whose tumors overexpress the ErbB2 protein.

Other anti-ErbB2 antibodies with various properties have been described in Tagliabue et al. *Int. J. Cancer* 47:933–937 (1991); McKenzie et al. *Oncogene* 4:543–548 (1989); Maier et al. *Cancer Res.* 51:5361–5369 (1991); Bacus et al. *Molecular Carcinogenesis* 3:350–362 (1990); Stancovski et al. *PNAS (USA)* 88:8691–8695 (1991); Bacus et al. *Cancer Research* 52:2580–2589 (1992); Xu et al *Int. J. Cancer* 53:401–408 (1993); WO94/00136; Kasprzyk et al. *Cancer Research* 52:2771–2776 (1992); Hancock et al. *Cancer Res.* 51:4575–4580 (1991); Shawver et al. *Cancer Res.* 54:1367–1373(1994); Arteaga et al. *Cancer Res.* 54:3758–3765 (1994); Harwerth et al. *J. Biol. Chem.* 267:15160–15167 (1992); U.S. Pat. No. 5,783,186; and Klapper et al. *Oncogene* 14:2099–2109 (1997).

Homology screening has resulted in the identification of two other ErbB receptor family members; ErbB3 (U.S. Pat.

Nos. 5,183,884 and 5,480,968 as well as Kraus et al. *PNAS (USA)* 86:9193–9197 (1989)) and ErbB4 (EP Pat Appln No 599,274; Plowman et al., *Proc. Nail. Acad. Sci. USA,* 90:1746–1750 (1993); and Plowman et al, *Nature,* 366:473–475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al. *Breast Cancer Research and Treatment* 35: 115–132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235–257 (1994)). A family of heregulin proteins resulting from alternative splicing of a single gene are ligands for ErbB3 and ErbB4. The heregulin family includes alpha, beta and gamma heregulins (Holmes et al., *Science,* 256:1205–1210 (1992); U.S. Pat. No. 5,641,869; and Schaefer et al. *Oncogene* 15:1385–1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235–257 (1994); Lemke, G. *Molec. & Cell. Neurosci.* 7:247–262 (1996) and Lee et al. *Pharm. Rev.* 47:51–85 (1995). Recently three additional ErbB ligands were identified; neuregulin-2 (NRG-2) which is reported to bind either ErbB3 or ErbB4 (Chang et al. *Nature* 387 509–512 (1997); and Carraway et al *Nature* 387:512–516 (1997)); neuregulin-3 which binds ErbB4 (Zhang et al. *PNAS* (USA) 94(18):9562–7 (1997)); and neuregulin-4 which binds ErbB4 (Harari et al. *Oncogene* 18:2681–89 (1999)) HB-EGF, betacellulin and epiregulin also bind to ErbB4.

While EGF and TGFα do not bind ErbB2, EGF stimulates EGFR and ErbB2 to form a heterodimer, which activates EGFR and results in transphosphorylation of ErbB2 in the heterodimer. Dimerization and/or transphosphorylation appears to activate the ErbB2 tyrosine kinase. See Earp et al., supra. Likewise, when ErbB3 is co-expressed with ErbB2, an active signaling complex is formed and antibodies directed against ErbB2 are capable of disrupting this complex (Sliwkowski et al., *J. Biol. Chem.,* 269(20): 14661–14665 (1994)). Additionally, the affinity of ErbB3 for heregulin (HRG) is increased to a higher affinity state when co-expressed with ErbB2. See also, Levi et al., *Journal of Neuroscience* 15: 1329–1340 (1995); Morrissey et al., *Proc. Nat. Acad. Sci. USA* 92: 1431–1435 (1995); and Lewis et al., *Cancer Res.,* 56:1457–1465 (1996) with respect to the ErbB2–ErbB3 protein complex. ErbB4, like ErbB3, forms an active signaling complex with ErbB2 (Carraway and Cantley, *Cell* 78:5–8 (1994)).

SUMMARY OR THE INVENTION

In a first aspect, the present invention provides a method of treating cancer in a human, wherein the cancer expresses epidermal growth factor receptor (EGFR), comprising administering to the human a therapeutically effective amount of an antibody which binds ErbB2.

Various advantages in using an antibody which binds ErbB2 to treat such cancer, as opposed to EGFR-targeted drugs, are contemplated herein. In particular, EGFR is highly expressed in liver and skin and this provides an enormous sink for active drug where the drug binds to EGFR. In addition, skin toxicity has been observed for other EGFR-targeted drugs such as the chimeric anti-EGFR antibody C225 and the small molecule drug ZD1839 which binds EGFR. Antibodies which bind ErbB2 are anticipated to have a better safety profile than such drugs.

Where the antibody used for therapy herein blocks ligand activation of an ErbB receptor and/or has a biological characteristic of monoclonal antibody 2C4, further advantages are achieved. For example, while EGFR-targeted drugs interfere only with EGFR, the antibodies of particular interest herein (e.g. 2C4, including humanized and/or affinity matured variants thereof) will interfere with EGFR/ErbB2, ErbB3/ErbB4 and ErbB2/ErbB3 heterodimers. In addition, the antibodies herein that bind ErbB2 and block ligand activation of an ErbB receptor will be complementary to EGFR-targeted drugs, where EGFR-targeted drugs are not complementary to each other.

The invention further provides a method of treating cancer in a human, wherein the cancer is not characterized by overexpression of the ErbB2 receptor, comprising administering to the human a therapeutically effective amount of an antibody which binds to ErbB2 and blocks ligand activation of an ErbB receptor.

In addition, the present invention provides a method of treating hormone independent cancer in a human comprising administering to the human a therapeutically effective amount of an antibody which binds ErbB2 receptor, and blocks ligand activation of an ErbB receptor.

The invention further provides a method of treating cancer in a human comprising administering to the human therapeutically effective amounts of (a) a first antibody which binds ErbB2 and inhibits growth of cancer cells which overexpress ErbB2; and (b) a second antibody which binds ErbB2 and blocks ligand activation of an ErbB receptor.

The invention also provides a method of treating a cancer in a human, wherein the cancer is selected from the group consisting of colon, rectal and colorectal cancer, comprising administering to the human a therapeutically effective amount of an antibody which binds ErbB2 and blocks ligand activation of an ErbB receptor.

In further embodiments, the invention provides articles of manufacture for use (among other things) in the above methods. For example, the invention provides an article of manufacture comprising a container and a composition contained therein, wherein the composition comprises an antibody which binds ErbB2, and further comprising a package insert indicating that the composition can be used to treat cancer which expresses epidermal growth factor receptor (EGFR).

The invention additionally pertains to an article of manufacture comprising a container and a composition contained therein, wherein the composition comprises an antibody which binds ErbB2 and blocks ligand activation of an ErbB receptor, and further comprising a package insert indicating that the composition can be used to treat cancer, wherein the cancer is not characterized by overexpression of the ErbB2 receptor.

Also, the invention relates to an article of manufacture comprising a container and a composition contained therein, wherein the composition comprises an antibody which binds ErbB2 and blocks ligand activation of an ErbB receptor, and further comprising a package insert indicating that the composition can be used to treat hormone independent cancer.

In a further embodiment, an article of manufacture is provided which comprises (a) a first container with a composition contained therein, wherein the composition comprises a first antibody which binds ErbB2 and inhibits growth of cancer cells which overexpress ErbB2; and (b) a second container with a composition contained therein, wherein the composition comprises a second antibody which binds ErbB2 and blocks ligand activation of an ErbB receptor.

A further article of manufacture is provided which comprises a container and a composition contained therein, wherein the composition comprises an antibody which binds ErbB2 and blocks ligand activation of an ErbB receptor, and further comprises a package insert indicating that the composition can be used to treat a cancer selected from the group consisting of colon, rectal and colorectal cancer.

The invention additionally provides: a humanized antibody which binds ErbB2 and blocks ligand activation of an ErbB receptor; a composition comprising the humanized antibody and a pharmaceutically acceptable carrier; and an immunoconjugate comprising the humanized antibody conjugated with a cytotoxic agent.

Moreover, the invention provides isolated nucleic acid encoding the humanized antibody; a vector comprising the nucleic acid; a host cell comprising the nucleic acid or the vector; as well as a process of producing the humanized antibody comprising culturing a host cell comprising the nucleic acid so that the nucleic acid is expressed and, optionally, further comprising recovering the humanized antibody from the host cell culture (e.g. from the host cell culture medium).

The invention further pertains to an immunoconjugate comprising an antibody which binds ErbB2 conjugated to one or more calicheamicin molecules, and the use of such conjugates for treating ErbB2 expressing cancer, e.g., ErbB2 overexpressing cancer, in a human. Preferably, the antibody in the conjugate is monoclonal antibody 4D5, e.g., humanized 4D5 (and preferably huMAb4D5-8 (HERCEPTIN®); or monoclonal antibody 2C4, e.g., humanized 2C4. The antibody in the immunoconjugate may be an intact antibody (e.g., an intact IgG$_1$ antibody) or an antibody fragment (e.g. a Fab, F(ab)$_2$, diabody etc).

BRIEF DESCRIPTION OF THE DRAWINGS

FIGS. 1A and 1B depict epitope mapping of residues 22–645 within the extracellular domain (ECD) of ErbB2 (amino acid sequence, including signal sequence, shown in FIG. 1A; SEQ ID NO:13) as determined by truncation mutant analysis and site-directed mutagenesis (Nakamura et al. *J. of Virology* 67(10):6179–6191 (1993); and Renz et al. *J. Cell Biol.* 125(6): 1395–1406 (1994)). The various ErbB2-ECD truncations or point mutations were prepared from cDNA using polymerase chain reaction technology. The ErbB2 mutants were expressed as gD fusion proteins in a mammalian expression plasmid. This expression plasmid uses the cytomegalovirus promoter/enhancer with SV40 termination and polyadenylation signals located downstream of the inserted cDNA. Plasmid DNA was transfected into 293 cells. One day following transfection, the cells were metabolically labeled overnight in methionine and cysteine-free, low glucose DMEM containing 1% dialyzed fetal bovine serum and 25 $\mu$Ci each of $^{35}$S methionine and $^{35}$S cysteine. Supernatants were harvested and either the anti-ErbB2 monoclonal antibodies or control antibodies were added to the supernatant and incubated 24 hours at 4° C. The complexes were precipitated, applied to a 10–20% Tricine SDS gradient gel and electrophoresed at 100 V. The gel was electroblotted onto a membrane and analyzed by autoradiography. As shown in FIG. 1B, the anti-ErbB2 antibodies 7C2, 7F3, 2C4, 7D3, 3E8, 4D5, 2H11 and 3H4 bind various ErbB2 ECD epitopes.

FIG. 2A shows dose-response curves for 2C4 or 7F3 inhibition of HRG stimulation of tyrosine phosphorylation. FIG. 2B shows dose-response curves for the inhibition of $^{125}$I-labeled rHRGβ1$_{177-244}$ binding to MCF7 cells by 2C4 or 7F3.

FIGS. 5A and 5B show the effect of monoclonal antibody 2C4, HERCEPTIN® antibody or an anti-EGFR antibody on heregulin (HRG) dependent association of ErbB2 with ErbB3 in MCF7 cells expressing low/normal levels of ErbB2 (FIG. 5A) and SK-BR-3 cells expressing high levels of ErbB2 (FIG. 5B); see Example 2 below.

FIG. 6A shows inhibition of $^{125}$I-HRG binding to MCF7 cells by chimeric 2C4 Fab or intact murine monoclonal antibody 2C4. MCF7 cells were seeded in 24-well plates (1×10$^5$ cells/well) and grown to about 85% confluency for two days. Binding experiments were conducted as described in Lewis et al. *Cancer Research* 56:1457–1465 (1996). FIG. 6B depicts inhibition of rHRGβ1 activation of p180 tyrosine phosphorylation in MCF7 cells performed as described in Lewis et al. *Cancer Research* 56:1457–1465 (1996).

FIGS. 7A and 7B depict alignments of the amino acid sequences of the variable light (V$_L$) (FIG. 7A) and variable heavy (V$_H$) (FIG. 7B) domains of murine monoclonal antibody 2C4 (SEQ ID Nos. 1 and 2, respectively); V$_L$ and V$_H$ domains of humanized 2C4 version 574 (SEQ ID Nos. 3 and 4, respectively), and human V$_L$ and V$_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

DETAILED DESCRIPTION OF THE PREFERRED EMBODIMENTS

I. Definitions

Figure 1B:
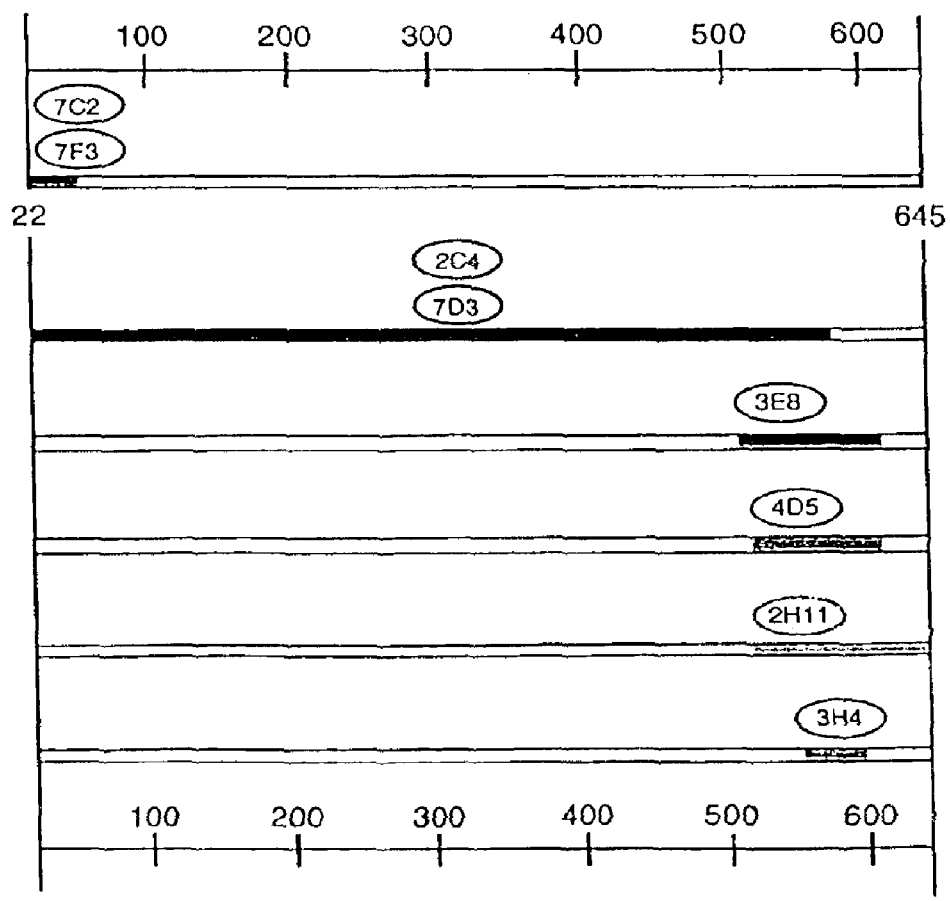

An "ErbB receptor" is a receptor protein tyrosine kinase which belongs to the ErbB receptor family and includes EGFR, ErbB2, ErbB3 and ErbB4 receptors and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably the ErbB receptor is native sequence human ErbB receptor.

The terms "ErbB I", "epidermal growth factor receptor" and "EGFR" are used interchangeably herein and refer to EGFR as disclosed, for example, in Carpenter et al. *Ann. Rev. Biochem.* 56:881–914 (1987), including naturally occurring mutant forms thereof (e.g. a deletion mutant EGFR as in Humphrey et al *PNAS* (USA) 87:4207–4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497–6501 (1985) and Yamamoto et al. *Nature* 319:230–234 (1986) (Genebank accession number X03363). The term "erbB2" refers to the gene encoding human ErbB2 and "neu" refers to the gene encoding rat p185$^{neu}$. Preferred ErbB2 is native sequence human ErbB2.

"ErbB3" and "HER3" refer to the receptor polypeptide as disclosed, for example, in U.S. Pat. Nos. 5,183,884 and 5,480,968 as well as Kraus et al. *PNAS* (USA) 86:9193–9197 (1989).

The terms "ErbB4" and "HER4" herein refer to the receptor polypeptide as disclosed, for example, in EP Pat Appln No 599,274; Plowman et al., *Proc. Natl. Acad. Sci. USA,* 90:1746–1750 (1993); and Plowman et al., *Nature,* 366:473–475 (1993), including isoforms thereof, e.g., as disclosed in WO99/19488, published Apr. 22, 1999.

By "ErbB ligand" is meant a polypeptide which binds to and/or activates an ErbB receptor. The ErbB ligand of particular interest herein is a native sequence human ErbB ligand such as epidermal growth factor (EGF) (Savage et al., *J. Biol. Chem.* 247:7612–7621 (1972)); transforming growth factor alpha (TGF-α) (Marquardt et al., *Science* 223:1079–1082 (1984)); amphiregulin also known as schwanoma or keratinocyte autocrine growth factor (Shoyab et al. *Science* 243:1074–1076(1989); Kimura et al. *Nature* 348:257–260(1990); and Cook er al. *Mol. Cell. Biol.* 11:2547–2557 (1991)); betacellulin (Shing et al., *Science* 259:1604–1607 (1993); and Sasada et al. *Biochem. Biophys. Res. Commun.* 190:1173(1993)); heparin-binding epidermal growth factor (HB-EGF)(Higashiyama et al., *Science* 251:936–939(1991)); epiregulin (Toyoda et al., *J. Biol. Chem.* 270:7495–7500(1995); and Komurasaki et al. *Oncogene* 15:2841–2848 (1997)); a heregulin (see below); neuregulin-2 (NRG-2) (Carraway et al., *Nature* 387:512–516(1997)); neuregulin-3 (NRG-3) (Zhang et al., *Proc. Natl. Acad. Sci.* 94:9562–9567(1997)); neuregulin-4 (NRG-4) (Harari et al. *Oncogene* 18:2681–89 (1999)) or cripto (CR-1) (Kannan et al. *J. Biol. Chem.* 272(6):3330–3335 (1997)). ErbB ligands which bind EGFR include EGF, TGF-α, amphiregulin, betacellulin, HB-EGF and epiregulin. ErbB ligands which bind ErbB3 include heregulins. ErbB ligands capable of binding ErbB4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362:312–318 (1993). Examples of heregulins include heregulin-α, heregulin-β1, heregulin-β2 and heregulin-β3 (Holmes er al., *Science,* 256:1205–1210(1992); and U.S. Pat. No. 5,641,869); neu differentiation factor (NDF) (Peles et al. *Cell* 69: 205–216 (1992)); acetylcholine receptor-inducing activity (ARIA) (Falls et al. *Cell* 72:801–815 (1993)); glial growth factors (GGFs) (Marchionni et al., *Nature,* 362:312–318(1993)); sensory and motor neuron derived factor (SMDF) (Ho et al. *J. Biol. Chem.* 270:14523–14532 (1995)); γ-heregulin (Schaefer et al. *Oncogene* 15:1385–1394 (1997)). The term includes biologically active fragments and/or amino acid sequence variants of a native sequence HRG polypeptide, such as an EGF-like domain fragment thereof (e.g. HRGβ1$_{177-244}$).

An "ErbB hetero-oligomer" herein is a noncovalently associated oligomer comprising at least two different ErbB receptors. Such complexes may form when a cell expressing two or more ErbB receptors is exposed to an ErbB ligand and can be isolated by immunoprecipitation and analyzed by SDS-PAGE as described in Sliwkowski et al., *J. Biol. Chem.,* 269(20):14661–14665 (1994), for example. Examples of such ErbB hetero-oligomers include EGFR-ErbB2, ErbB2–ErbB3 and ErbB3–ErbB4 complexes. Moreover, the ErbB hetero-oligomer may comprise two or more ErbB2 receptors combined with a different ErbB receptor, such as ErbB3, ErbB4 or EGFR. Other proteins, such as a cytokine receptor subunit (e.g. gp130) may be included in the hetero-oligomer.

By "ligand activation of an ErbB receptor" is meant signal transduction (e.g. that caused by an intracellular kinase domain of an ErbB receptor phosphorylating tyrosine residues in the ErbB receptor or a substrate polypeptide) mediated by ErbB ligand binding to a ErbB hetero-oligomer comprising the ErbB receptor of interest. Generally, this will involve binding of an ErbB ligand to an ErbB hetero-oligomer which activates a kinase domain of one or more of the ErbB receptors in the hetero-oligomer and thereby results in phosphorylation of tyrosine residues in one or more of the ErbB receptors and/or phosphorylation of tyrosine residues in additional substrate polypeptides(s). ErbB receptor activation can be quantified using various tyrosine phosphorylation assays.

A "native sequence" polypeptide is one which has the same amino acid sequence as a polypeptide (e.g., ErbB receptor or ErbB ligand) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70% homology with at least one receptor binding domain of a native ErbB ligand or with at least one ligand binding domain of a native ErbB receptor, and preferably, they will be at least about 80%, more preferably at least about 90% homologous with such receptor or ligand binding domains. The amino acid sequence variants possess substitutions, deletions, and/or insertions at certain positions within the amino acid sequence of the native amino acid sequence.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624–628 (1991) and Marks et al., *J. Mol. Biol.,* 222:581–597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA,* 81:6851–6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457–92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652–656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203–234 (1997)). FcRs are reviewed in Ravetch and Kinet, Annu. Rev. Immunol 9:457–92 (1991); Capel et al., *Immunomethods* 4:25–34 (1994); and de Haas et al., *J. Lab. Clin. Med.* 126:330–41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 2632 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer- Verlag, New York, pp. 269–315 (1994). Anti-ErbB2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al., *Nature* 332:323–329(1988); and Presta, *Curr. Op. Struct. Biol.* 2:593–596 (1992).

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO93/21319) and humanized 2C4 antibodies as described hereinbelow.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other protcinaceous or nonproteinaceous solutes. In preferred embodiments, the antibody will be purified (I) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. ErbB2 antigen, is one capable of binding that antigen with sufficient affinity such that the antibody is useful as a therapeutic agent in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. *Nature* 312:513 (1984) and Drebin et al., *Nature* 312:545–548(1984).

An antibody which "blocks" ligand activation of an ErbB receptor is one which reduces or prevents such activation as hereinabove defined, wherein the antibody is able to block ligand activation of the ErbB receptor substantially more effectively than monoclonal antibody 4D5, e.g. about as effectively as monoclonal antibodies 7F3 or 2C4 or Fab fragments thereof and preferably about as effectively as monoclonal antibody 2C4 or a Fab fragment thereof. For example, the antibody that blocks ligand activation of an ErbB receptor may be one which is about 50–100% more effective than 4D5 at blocking formation of an ErbB hetero-oligomer. Blocking of ligand activation of an ErbB receptor can occur by any means, e.g. by interfering with: ligand binding to an ErbB receptor, ErbB complex formation, tyrosine kinase activity of an ErbB receptor in an ErbB complex and/or phosphorylation of tyrosine kinase residue (s) in or by an ErbB receptor. Examples of antibodies which block ligand activation of an ErbB receptor include monoclonal antibodies 2C4 and 7F3 (which block HRG activation of ErbB2/ErbB3 and ErbB2/ErbB4 hetero-oligomers; and EGF, TGF-α, amphiregulin, HB-EGF and/or epiregulin activation of an EGFR/ErbB2 hetero-oligomer); and L26, L96 and L288 antibodies (Klapper et al. *Oncogene* 14:2099–2109(1997)), which block EGF and NDF binding to T47D cells which express EGFR, ErbB2, ErbB3 and ErbB4.

An antibody having a "biological characteristic" of a designated antibody, such as the monoclonal antibody designated 2C4, is one which possesses one or more of the biological characteristics of that antibody which distinguish it from other antibodies that bind to the same antigen (e.g. ErbB2). For example, an antibody with a biological characteristic of 2C4 may block HRG activation of an ErbB hetero-oligomer comprising ErbB2 and ErbB3 or ErbB4; block EGF, TGF-α, HB-EGF, epiregulin and/or amphiregulin activation of an ErbB receptor comprising EGFR and ErbB2; block EGF, TGF-α and/or HRG mediated activation of MAPK, and/or bind the same epitope in the extracellular domain of ErbB2 as that bound by 2C4 (e.g. which blocks binding of monoclonal antibody 2C4 to ErbB2).

Unless indicated otherwise, the expression "monoclonal antibody 2C4" refers to an antibody that has antigen binding residues of, or derived from, the murine 2C4 antibody of the Examples below. For example, the monoclonal antibody 2C4 may be murine monoclonal antibody 2C4 or a variant thereof, such as humanized antibody 2C4, possessing antigen binding amino acid residues of murine monoclonal antibody 2C4. Examples of humanized 2C4 antibodies are provided in Example 3 below. Unless indicated otherwise, the expression "rhuMAb 2C4" when used herein refers to an antibody comprising the variable light ($V_L$) and variable heavy ($V_H$) sequences of SEQ ID Nos. 3 and 4, respectively, fused to human light and heavy IgG1 (non-A allotype) constant region sequences optionally expressed by a Chinese Hamster Ovary (CHO) cell.

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5, possessing antigen binding residues of murine monoclonal antibody 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337, with huMAb4D5-8 (HERCEPTIN®) being a preferred humanized 4D5 antibody.

A "growth inhibitory agent" when used herein refers to a compound or composition which inhibits growth of a cell, especially an ErbB expressing cancer cell either in vitro or in vivo. Thus, the growth inhibitory agent may be one which significantly reduces the percentage of ErbB expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13.

Examples of "growth inhibitory" antibodies are those which bind to ErbB2 and inhibit the growth of cancer cells overexpressing ErbB2. Preferred growth inhibitory anti-ErbB2 antibodies inhibit growth of SK-BR-3 breast tumor cells in cell culture by greater than 20%, and preferably greater than 50% (e.g. from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is monoclonal antibody 4D5, e.g., humanized 4D5.

An antibody which "induces cell death" is one which causes a viable cell to become nonviable. The cell is generally one which expresses the ErbB2 receptor, especially where the cell overexpresses the ErbB2 receptor. Preferably, the cell is a cancer cell, e.g. a breast, ovarian, stomach, endometrial, salivary gland, lung, kidney, colon, thyroid, pancreatic or bladder cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1–11 (1995)) or 7AAD can be assessed relative to untreated cells. Preferred cell death-inducing antibodies are those which induce PI uptake in the PI uptake assay in BT474 cells (see below).

An antibody which "induces apoptosis" is one which induces programmed cell, death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the ErbB2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Sometimes the pro-apoptotic antibody will be one which further blocks ErbB ligand activation of an ErbB receptor (e.g. 7F3 antibody); i.e. the antibody shares a biological characteristic with monoclonal antibody 2C4. In other situations, the antibody is one which does not significantly block ErbB ligand activation of an ErbB receptor (e.g. 7C2). Further, the antibody may be one like 7C2 which, while inducing apoptosis, does not induce a large reduction in the percent of cells in S phase (e.g. one which only induces about 0–10% reduction in the percent of these cells relative to control).

The "epitope 2C4" is the region in the extracellular domain of ErbB2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 2C4 epitope of ErbB2 (e.g. any one or more residues in the region from about residue 22 to about residue 584 of ErbB2, inclusive; see FIGS. 1A–B).

The "epitope 4D5" is the region in the extracellular domain of ErbB2 to which the antibody 4D5 (ATCC CRL 10463) binds. This epitope is close to the transmembrane domain of ErbB2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of ErbB2 (e.g. any one or more residues in the region from about residue 529 to about residue 625, inclusive; see FIGS. 1A–B).

The "epitope 3H4" is the region in the extracellular domain of ErbB2 to which the antibody 3H4 binds. This epitope includes residues from about 541 to about 599, inclusive, in the amino acid sequence of ErbB2 extracellular domain; see FIGS. 1A–B.

The "epitope 7C2/7F3" is the region at the N terminus of the extracellular domain of ErbB2 to which the 7C2 and/or 7F3 antibodies (each deposited with the ATCC, see below)

bind. To screen for antibodies which bind to the 7C2 nF3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2 nF3 epitope on ErbB2 (e.g. any one or more of residues in the region from about residue 22 to about residue 53 of ErbB2; see FIGS. 1A–B).

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the anti-ErbB2 antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer "characterized by excessive activation" of an ErbB receptor is one in which the extent of ErbB receptor activation in cancer cells significantly exceeds the level of activation of that receptor in non-cancerous cells of the same tissue type. Such excessive activation may result from overexpression of the ErbB receptor and/or greater than normal levels of an ErbB ligand available for activating the ErbB receptor in the cancer cells. Such excessive activation may cause and/or be caused by the malignant state of a cancer cell. In some embodiments, the cancer will be subjected to a diagnostic or prognostic assay to determine whether amplification and/or overexpression of an ErbB receptor is occurring which results in such excessive activation of the ErbB receptor. Alternatively, or additionally, the cancer may be subjected to a diagnostic or prognostic assay to determine whether amplification and/or overexpression an ErbB ligand is occurring in the cancer which attributes to excessive activation of the receptor. In a subset of such cancers, excessive activation of the receptor may result from an autocrine stimulatory pathway.

In an "autocrine" stimulatory pathway, self stimulation occurs by virtue of the cancer cell producing both an ErbB ligand and its cognate ErbB receptor. For example, the cancer may express or overexpress EGFR and also express or overexpress an EGFR ligand (e.g. EGF, TGF-α, or HB-EGF). In another embodiment, the cancer may express or overexpress ErbB2 and also express or overexpress a heregulin (e.g. γ-HRG).

A cancer which "overexpresses" an ErbB receptor is one which has significantly higher levels of an ErbB receptor, such as ErbB2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein presenton the surface of a cell (e.g. via an immunohistochemistry assay; IHC). Alternatively, or additionally, one may measure levels of ErbB-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). One may also study ErbB receptor overexpression by measuring shed antigen (e.g., ErbB extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132 73–80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which is "not characterized by overexpression of the ErbB2 receptor" is one which, in a diagnostic assay, does not express higher than normal levels of ErbB2 receptor compared to a noncancerous cell of the same tissue type.

A cancer which "overexpresses" an ErbB ligand is one which produces significantly higher levels of that ligand compared to a noncancerous cell of the same tissue type. Such overexpression may be caused by gene amplification or by increased transcription or translation. Overexpression of the ErbB ligand may be determined diagnostically by evaluating levels of the ligand (or nucleic acid encoding it) in the patient, e.g. in a tumor biopsy or by various diagnostic assays such as the IHC, FISH, southern blotting, PCR or in vivo assays described above.

A "hormone independent" cancer is one in which proliferation thereof is not dependent on the presence of a hormone which binds to a receptor expressed by cells in the cancer. Such cancers do not undergo clinical regression upon administration of pharmacological or surgical strategies that reduce the hormone concentration in or near the tumor. Examples of hormone independent cancers include androgen independent prostate cancer, estrogen independent breast cancer, endometrial cancer and ovarian cancer. Such cancers may begin as hormone dependent tumors and progress from a hormone-sensitive stage to a hormone-refractory tumor following anti-hormonal therapy.

The term "cytotoxic agent" as used herein refers to a substance that inhibits or prevents the function of cells and/or causes destruction of cells. The term is intended to include radioactive isotopes (e.g. $At^{211}$, $I^{131}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR (see WO98/50433, Abgenix). The anti-EGFR antibody may be conjugated with a cyotoxic agent, thus generating an immunoconjugate (see, e.g., EP659,439A2, Merck Patent GmbH). Examples of small molecules that bind to EGFR include ZD1839 (Astra Zeneca), CP-358774 (OSI/Pfizer) and AG1478.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoictin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375–382, 615th Meeting Belfast (1986) and Stella et al., "Prodrugs: A Chemical Approach to Targeted Drug Delivery," Directed Drug Delivery, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

A "cardioprotectant" is a compound or composition which prevents or reduces myocardial dysfunction (i.e. cardiomyopathy and/or congestive heart failure) associated with administration of a drug, such as an anthracycline antibiotic and/or an anti-ErbB2 antibody, to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. *The Annals of Pharmacotherapy* 28:1063–1072 (1994)); a lipid-lowering agent and/or anti-oxidant such as probucol (Singal et al. *J. Mol. Cell Cardiol.* 27:1055–1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino) propylphosphorothioic acid (WR-151327), see Green et al. *Cancer Research* 54:738–741 (1994); digoxin (Bristow, M. R. In: Bristow MR, ed. Drug-Induced Heart Disease. New York: Elsevier 191–215 (1980)); beta-blockers such as metoprolol (Hjalmarson et al. *Drugs* 47: Suppl 4:31–9 (1994); and Shaddy et al. *Am. Heart J.* 129:197–9(1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., *Anticancer Res.* 13:1607–1612 (1993)); selenoorganic compounds such as P251 (Elbesen); and the like.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Production of Anti-ErbB2 Antibodies

A description follows as to exemplary techniques for the production of the antibodies used in accordance with the present invention, The ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g. NIH-3T3 cells transformed to overexpress ErbB2; or a carcinoma cell line such as SK-BR-3 cells, see Stancovski et al. *PNAS* (USA) 88:8691–8695 (1991)) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and R are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001(1984); and Brodeur et al. *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Plückthun, *Immunol. Revs.*, 130:151–188 (1992).

In a further embodiment, monoclonal antibodies or antibody fragments can be isolated from antibody phage libraries generated using the techniques described in McCafferty et al., *Nature*, 348:552–554 (1990). Clackson et al. *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623(1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 3 below describes production of exemplary humanized anti-ErbB2 antibodies which bind ErbB2 and block ligand activation of an ErbB receptor. The humanized antibody of particular interest herein blocks EGF, TGF-α and/or HRG mediated activation of MAPK essentially as effectively as murine monoclonal antibody 2C4 (or a Fab fragment thereof) and/or binds ErbB2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO:4.

The humanized antibody may comprise variable light domain complementarity determining residues KASQDVSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO:3.

The present application also contemplates affinity matured antibodies which bind ErbB2 and block ligand activation of an ErbB receptor. The parent antibody may be a human antibody or a humanized antibody, e.g., one comprising the variable light and/or heavy sequences of SEQ ID Nos. 3 and 4, respectively (i.e. variant 574). The affinity matured antibody preferably binds to ErbB2 receptor with an affinity superior to that of murine 2C4 or variant 574 (e.g. from about two or about four fold, to about 100 fold or about 1000 fold improved affinity, e.g. as assessed using a ErbB2- extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255–258 (1993); Bruggermann et al., Year in Immuno., 7:33 (1993); and U.S. Pat. Nos. 5,591,669, 5,589,369 and 5,545,807.

Alternatively, phage display technology (McCafferty et al., Nature 348:552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., Current Opinion in Structural Biology 3:564–571(1993). Several sources of V-gene segments can be used for phage display. Clackson et al., Nature, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581–597 (1991), or Griffith et al., EMBO J. 12:725–734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human anti-ErbB2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107–117(1992); and Brennan et al., Science, 229:81(1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab)_2$ fragments (Carter et al., Bio/Technology 10: 163–167 (1992)). According to another approach, $F(ab)_2$ fragments can be isolated directly from recombinant host cell culture. Other techniques for the production of antibody fragments will be apparent to the skilled practitioner. In other embodiments, the antibody of choice is a single chain Fv fragment (scFv). See WO93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the ErbB2 protein. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. These antibodies possess an ErbB2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab)$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immunobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab)$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147:60 (1991).

(vii) Other Amino Acid Sequence Modifications

Amino acid sequence modification(s) of the anti-ErbB2 antibodies described herein are contemplated. For example, it may be desirable to improve the binding affinity and/or other biological properties of the antibody. Amino acid sequence variants of the anti-ErbB2 antibody are prepared by introducing appropriate nucleotide changes into the anti-ErbB2 antibody nucleic acid, or by peptide synthesis. Such modifications include, for example, deletions from, and/or insertions into and/or substitutions of, residues within the amino acid sequences of the anti-ErbB2 antibody. Any combination of deletion, insertion, and substitution is made to arrive at the final construct, provided that the final construct possesses the desired characteristics. The amino acid changes also may alter post-translational processes of the anti-ErbB2 antibody, such as changing the number or position of glycosylation sites.

A useful method for identification of certain residues or regions of the anti-ErbB2 antibody that are preferred locations for mutagenesis is called "alanine scanning mutagenesis" as described by Cunningham and Wells Science, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with ErbB2 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-ErbB2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-ErbB2 antibody with an N-terminal methionyl residue or the antibody fused to a cytotoxic polypeptide. Other insertional variants of the anti-ErbB2 antibody molecule include the fusion to the N- or C-terminus of the anti-ErbB2 antibody to an enzyme (e.g. for ADEPT) or a polypeptide which increases the serum half-life of the antibody.

Another type of variant is an amino acid substitution variant. These variants have at least one amino acid residue in the anti-ErbB2 antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-ErbB2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human ErbB2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-ErbB 2 anti body are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-ErbB2 antibody.

It may be desirable to modify the antibody of the invention with respect to effector function, e.g. so as to enhance antigen-dependent cell-mediated cyotoxicity (ADCC) and/or complement dependent cytoloxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al. *Cancer Research* 53:2560–2565 (1993). Alternatively, an antibody can be engineered which has dual Fc regions and may thereby have enhanced complement lysis and ADCC capabilities. See Stevenson et al. *Anti-Cancer Drug Design* 3:219–230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(viii) Screening for Antibodies with the Desired Properties

Techniques for generating antibodies have been described above. One may further select antibodies with certain biological characteristics, as desired.

To identify an antibody which blocks ligand activation of an ErbB receptor, the ability of the antibody to block ErbB ligand binding to cells expressing the ErbB receptor (e.g. in conjugation with another ErbB receptor with which the ErbB receptor of interest forms an ErbB hetero-oligomer) may be determined. For example, cells naturally expressing, or transfected to express, ErbB receptors of the ErbB hetero-oligomer may be incubated with the antibody and then exposed to labeled ErbB ligand. The ability of the anti-ErbB2 antibody to block ligand binding to the ErbB receptor in the ErbB hetero-oligomer may then be evaluated.

For example, inhibition of HRG binding to MCF7 breast tumor cell lines by anti-ErbB2 antibodies may be performed using monolayer MCF7 cultures on ice in a 24-well-plate format essentially as described in Example 1 below. Anti-ErbB2 monoclonal antibodies may be added to each well and incubated for 30 minutes. $^{125}$I-labeled rHRGβ1$_{177-224}$ (25 pm) may then be added, and the incubation may be continued for 4 to 16 hours. Dose response curves may be prepared and an $IC_{50}$ value may be calculated for the antibody of interest. In one embodiment, the antibody which blocks ligand activation of an ErbB receptor will have an $IC_{50}$ for inhibiting HRG binding to MCF7 cells in this assay of about 50 nM or less, more preferably 10 nM or less. Where the antibody is an antibody fragment such as a Fab fragment, the $IC_{50}$ for inhibiting HRG binding to MCF7 cells in this assay may, for example, be about 100 nM or less, more preferably 50 nM or less.

Alternatively, or additionally, the ability of the anti-ErbB2 antibody to block ErbB ligand-stimulated tyrosine phosphorylation of an ErbB receptor present in an ErbB hetero-oligomer may be assessed. For example, cells endogenously expressing the ErbB receptors or transfected to expressed them may be incubated with the antibody and then assayed for ErbB ligand-dependent tyrosine phosphorylation activity using an anti-phospholyrosine monoclonal (which is optionally conjugated with a detectable label). The kinase receptor activation assay described in U.S. Pat. No. 5,766,863 is also available for determining ErbB receptor activation and blocking of that activity by an antibody.

In one embodiment, one may screen for an antibody which inhibits HRG stimulation of p180 tyrosine phosphorylation in MCF7 cells essentially as described in Example 1 below. For example, the MCF7 cells may be plated in 24-well plates and monoclonal antibodies to ErbB2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4–12% gradient gel (Novex) and then electrophoretically transferred to polyvinylidene difluoride membrane. Antiphosphotyrosine (at 1 μg/ml) immunoblots may be developed, and the intensity of the predominant reactive band at $M_r$-180,000 may be quantified by reflectance densitometry. The antibody selected will preferably significantly inhibit HRG stimulation of p180 tyrosine phosphorylation to about 0–35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of an ErbB receptor will have an $IC_{50}$ for inhibiting HRG stimulation of p 180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385–1394 (1997). According to this assay, MDA-MB-175 cells may treated with an anti-ErbB2 monoclonal antibody (10 μg/mL) for 4 days and stained with crystal violet. Incubation with an anti-ErbB2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the anti-ErbB2 antibody of interest may block heregulin dependent association of ErbB2 with ErbB3 in both MCF7 and SK-BR-3 cells as determined in a co-immunoprecipitation experiment such as that described in Example 2 substantially more effectively than monoclonal antibody 4D5, and preferably substantially more effectively than monoclonal antibody 7F3.

To identify growth inhibitory anti-ErbB2 antibodies, one may screen for antibodies which inhibit the growth of cancer cells which overexpress ErbB2. In one embodiment, the growth inhibitory antibody of choice is able to inhibit growth of SK-BR-3 cells in cell culture by about 20–100% and preferably by about 50–100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the anti-ErbB2 antibody is added per dish. After six days, the number of cells, compared to untreated cells are counted using an electronic COULTER™ cell counter. Those antibodies which inhibit growth of the SK-BR-3 cells by about 20–100% or about 50–100% may be selected as growth inhibitory antibodies.

To select for antibodies which induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Rockville, Md.)) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of $3 \times 10^6$ per dish in 100×20 mm dishes and allowed to attach overnight. The medium is then removed and replaced with fresh medium alone or medium containing 10 µg/ml of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in Ca binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a DNA staining assay using BT474 cells is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To screen for antibodies which bind to an epitope on ErbB2 bound by an antibody of interest, a routine cross-blocking assay such as that described in Antibodies, A Laboratory Manual, Cold Spring Harbor Laboratory, Ed Harlow and David Lane (1988), can be performed. Alternatively, or additionally, epitope mapping can be performed by methods known in the art (see, e.g. FIGS. 1A and 1B herein).

(ix) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (ie., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC 1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al Cancer Research 52: 127–131 (1992)) to generate a maytansinoid-antibody immunoconjugate.

Another immunoconjugate of interest comprises an anti-ErbB2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$, (Hinman et al. Cancer Research 53: 3336–3342 (1993) and Lode et al. Cancer Research 58: 2925–2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated anti-ErbB2 antibodies.

Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. Sec WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127–131 (1992)) may be used.

Alternatively, a fusion protein comprising the anti-ErbB2 antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs, β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457–458 (1987)). Antibody-abzyme conjugates can be prepared as described herein for delivery of the abzyme to a tumor cell population.

The enzymes of this invention can be covalently bound to the anti-ErbB2 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604–608 (1984)).

(xi) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-ErbB2 antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286–288 (1982) via a disulfide interchange reaction. A chemotherapeutic agent is optionally contained within the liposome. See Gabizon et al. *J. National Cancer Inst.* 81(19)1484 (1989).

III. Vectors, Host Cells and Recombinant Methods

The invention also provides isolated nucleic acid encoding the humanized anti-ErbB2 antibody, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The anti-ErbB2 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-ErbB2 antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g. the yeast invertase leader, a factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the anti-ErbB2 antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-ErbB2 antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-ErbB2 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al, Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of Kluyveromyces yeasts. Alternatively, an expression system for large-scale production of recombinant calf chymosin was reported for K. lactis Van den Berg, Bio/technology, 8:135 (1990). Stable multi-copy expression vectors for secretion of mature recombinant human serum albumin by industrial strains of Kluyveromyces have also been disclosed. Fleer et al, Bio/Technology, 9:968–975 (1991).

(iv) Promoter Component

Expression and cloning vectors usually contain a promoter that is recognized by the host organism and is operably linked to the anti-ErbB2 antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-ErbB2 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-ErbB2 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papillomavirus as a vector is disclosed in U.S. Pat. No. 4,419,446. A modification of this system is described in U.S. Pat. No. 4,601,978. See also Reyes et al., Nature 297:598–601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the anti-ErbB2 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, Nature 297:17–18 (1982) on enhancing elements for activation of eukaryotic promoters. The enhancer may be spliced into the vector at a position 5' or 3' to the anti-ErbB2 antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3, untranslated regions of eukaryotic or viral DNAs or cDNAs. These regions contain nucleotide segments transcribed as polyadenylated fragments in the untranslated portion of the mRNA encoding anti-ErbB2 antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include *eubacteria*, such as Gram-negative or Grain-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X11776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-ErbB2 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045). *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-ErbB2 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243–251 (1980)); monkey kidney cells (CV1 ATCC CCL 70); African green monkey kidney cells (VERO-76, ATCC CRL-1587); human cervical carcinoma cells HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. Annals N.Y. Acad. Sci. 383:44–68 (1982)); MRC 5 cells; FS4 cells; and a human hepatoma line (Hep G2).

Host cells are transformed with the above-described expression or cloning vectors for anti-ErbB2 antibody production and cultured in conventional nutrient media modified as appropriate for inducing promoters, selecting transformants, or amplifying the genes encoding the desired sequences.

(viii) Culturing the Host Cells

The host cells used to produce the anti-ErbB2 antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Anti-ErbB2 Antibody

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.54.5, preferably performed at low salt concentrations (e.g., from about 0–0.25M salt).

IV. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURON-ICS™ or polyethylene glycol (PEG). Preferred lyophilized anti-ErbB2 antibody formulations are described in WO 97/04801, expressly incorporated herein by reference.

The formulation herein may also contain more than one active compound as necessary for the particular indication being treated, preferably those with complementary activities that do not adversely affect each other. For example, it may be desirable to further provide antibodies which bind to EGFR, ErbB2 (e.g. an antibody which binds a different epitope on ErbB2), ErbB3, ErbB4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, EGFR-targeted drug, anti-angiogenic agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment with the Anti-ErbB2 Antibodies

It is contemplated that, according to the present invention, the anti-ErbB2 antibodies may be used to treat various diseases or disorders. Exemplary conditions or disorders include benign or malignant tumors; leukemias and lymphoid malignancies; other disorders such as neuronal, glial, astrocytal, hypothalamic, glandular, macrophagal, epithelial, stromal, blastocoelic, inflammatory, angiogenic and immunologic disorders.

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer will general ly comprise ErbB2-expressing cells, such that the anti-ErbB2 antibody herein is able to bind to the cancer. While the cancer may be characterized by overexpression of the ErbB2 receptor, the present application further provides a method for treating cancer which is not considered to be an ErbB2-overexpressing cancer. To determine ErbB2 expression in the cancer, various diagnostic/prognostic assays are available. In one embodiment, ErbB2 overexpression may be analyzed by IHC, e.g. using the HERCEPTEST® (Dako). Parrafin embedded tissue sections from a tumor biopsy may be subjected to the IHC assay and accorded a ErbB2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+scores for ErbB2 overexpression assessment may be characterized as not overexpressing ErbB2, whereas those tumors with 2+ or 3+scores may be characterized as overexpressing ErbB2.

Alternatively, or additionally, FISH assays such as the INFORM™ (sold by Ventana, Arizona) or PATHVISION™ (Vysis, Ill.) may be carried out on formalin-fixed, paraffin-embedded tumor tissue to determine the extent (if any) of ErbB2 overexpression in the tumor.

In one embodiment, the cancer will be one which expresses (and may overexpress) EGFR. Examples of cancers which may express/overexpress EGFR include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer to be treated herein may be one characterized by excessive activation of an ErbB receptor, e.g. EGFR. Such excessive activation may be attributable to overexpression or increased production of the ErbB receptor or an ErbB ligand. In one embodiment of the invention, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include the IHC, FISH and shed antigen assays described above. Alternatively, or additionally, levels of an ErbB ligand, such as TGF-α, in or associated with the tumor may be determined according to known procedures. Such assays may detect protein and/or nucleic acid encoding it in the sample to be tested. In one embodiment, ErbB ligand levels in the tumor may be determined using immunohistochemistry (IHC); see, for example, Scher et al. *Clin. Cancer Research* 1:545–550 (1995). Alternatively, or additionally, one may evaluate levels of ErbB ligand-encoding nucleic acid in the sample to be tested; e.g. via FISH, southern blotting, or PCR techniques.

Moreover, ErbB receptor or ErbB ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

Where the cancer to be treated is hormone independent cancer, expression of the hormone (e.g. androgen) and/or its cognate receptor in the tumor may be assessed using any of the various assays available, e.g. as described above. Alternatively, or additionally, the patient may be diagnosed as having hormone independent cancer in that they no longer respond to anti-androgen therapy.

In certain embodiments, an immunoconjugate comprising the anti-ErbB2 antibody conjugated with a cytotoxic agent is administered to the patient. Preferably, the immunoconjugate and/or ErbB2 protein to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The anti-ErbB2 antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-ErbB2 antibody. The combined administration includes coadministration, using separate formulations or a single pharmaceutical formulation, and consecutive administration in either order, wherein preferably there is a time period while both (or all) active agents simultaneously exert their biological activities.

In one preferred embodiment, the patient is treated with two different anti-ErbB2 antibodies. For example, the patient may be treated with a first anti-ErbB2 antibody which blocks ligand activation of an ErbB receptor or an antibody having a biological characteristic of monoclonal antibody 2C4 as well as a second anti-ErbB2 antibody which is growth inhibitory (e.g. HERCEPTIN®) or an anti-ErbB2 antibody which induces apoptosis of an ErbB2-overexpressing cell (e.g. 7C2, 7F3 or humanized variants thereof). Preferably such combined therapy results in a synergistic therapeutic effect. One may, for instance, treat the patient with HERCEPTIN® and thereafter treat with rhuMAb 2C4, e.g. where the patient does not respond to HERCEPTIN® therapy. In another embodiment, the patient may first be treated with rhuMAb 2C4 and then receive HERCEPTIN® therapy. In yet a further embodiment, the patient may be treated with both rhuMAb 2C4 and HERCEPTIN® simultaneously.

It may also be desirable to combine administration of the anti-ErbB2 antibody or antibodies, with administration of an antibody directed against another tumor associated antigen. The other antibody in this case may, for example, bind to EGFR, ErbB3, ErbB4, or vascular endothelial growth factor (VEGF).

In one embodiment, the treatment of the present invention involves the combined administration of an anti-ErbB2 antibody (or antibodies) and one or more chemotherapeutic agents or growth inhibitory agents, including coadministration of cocktails of different chemotherapeutic agents. Preferred chemotherapeutic agents include taxanes (such as paclitaxel and docetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient.

Sometimes, it may be beneficial to also coadminister a cardioprotectant (to prevent or reduce myocardial dysfunction associated with the therapy) or one or more cytokines to the patient. One may also coadminister an EGFR-targeted drug or an anti-angiogenic agent. In addition to the above therapeutic regimes, the patient may be subjected to surgical removal of cancer cells and/or radiation therapy.

The anti-ErbB2 antibodies herein may also be combined with an EGFR-targeted drug such as those discussed above in the definitions section resulting in a complementary, and potentially synergistic, therapeutic effect.

Suitable dosages for any of the above coadministered agents are those presently used and may be lowered due to the combined action (synergy) of the agent and anti-ErbB2 antibody.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 $\mu$g/kg to 15 mg/kg (e.g. 0.1–20 mg/kg) of antibody is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 4 mg/kg, followed by a weekly maintenance dose of about 2 mg/kg of the anti-ErbB2 antibody. However, other dosage regimens may be useful. The progress of this therapy is easily monitored by conventional techniques and assays.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429–4432 (1987); and Wagner et al., *Proc. Natl. Acad. Sci. USA* 87:3410–3414 (1990). For review of the currently known gene marking and gene therapy protocols see Anderson et al., *Science* 256:808–813 (1992). See also WO 93/25673 and the references cited therein.

VI. Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-ErbB2 antibody. The label or package insert indicates that the composition is used for treating the condition of choice, such as cancer. In one embodiment, the label or package inserts indicates that the composition comprising the antibody which binds ErbB2 can be used to treat cancer which expresses an ErbB receptor selected from the group consisting of epidermal growth factor receptor (EGFR), ErbB3 and ErbB4, preferably EGFR. In addition, the label or package insert may indicate that the patient to be treated is one having cancer characterized by excessive activation of an ErbB receptor selected from EGFR, ErbB 3 or ErbB4. For example, the cancer may be one which overexpresses one of these receptors and/or which overexpresses an ErbB ligand (such as TGF-α). The label or package insert may also indicate that the composition can be used to treat cancer, wherein the cancer is not characterized by overexpression of the ErbB2 receptor. For example, whereas the present package insert for HERCEPTIN® indicates that the antibody is used to treat patients with metastatic breast cancer whose tumors overexpress the ErbB2 protein, the package insert herein may indicate that the antibody or composition is used to treat cancer regardless of the extent of ErbB2 overexpression. In other embodiments, the package insert may indicate that the antibody or composition can be used to treat breast cancer (e.g. metastatic breast cancer); hormone independent cancer; prostate cancer, (e.g. androgen independent prostate cancer); lung cancer (e.g. non-small cell lung cancer); colon, rectal or colorectal cancer; or any of the other diseases or disorders disclosed herein. Moreover, the article of manufacture may comprise (a) a first container with a composition contained therein, wherein the composition comprises a first antibody which binds ErbB2 and inhibits growth of cancer cells which overexpress ErbB2; and (b) a second container with a composition contained therein, wherein the composition comprises a second antibody which binds ErbB2 and blocks ligand activation of an ErbB receptor. The article of manufacture in this embodiment of the invention may further comprises a package insert indicating that the first and second antibody compositions can be used to treat cancer. Moreover, the package insert may instruct the user of the composition (comprising an antibody which binds ErbB2 and blocks ligand activation of an ErbB receptor) to combine therapy with the antibody and any of the adjunct therapies described in the preceding section (e.g. a chemotherapeutic agent, an EGFR-targeted drug, an anti-angiogenic agent, an anti-hormonal compound, a cardioprotectant and/or a cytokine). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

VII. Non-Therapeutic Uses for the Anti-ErbB2 Antibody

The antibodies (e.g. the humanized anti-ErbB2 antibodies) of the invention have further non-therapeutic applications.

For example, the antibodies may be used as affinity purification agents. In this process, the antibodies are immobilized on a solid phase such a Sephadex resin or filter paper, using methods well known in the art. The immobilized antibody is contacted with a sample containing the ErbB2 protein (or fragment thereof) to be purified, and thereafter the support is washed with a suitable solvent that will remove substantially all the material in the sample except the ErbB2 protein, which is bound to the immobilized antibody. Finally, the support is washed with another suitable solvent, such as glycine buffer, pH 5.0, that will release the ErbB2 protein from the antibody.

Anti-ErbB2 antibodies may also be useful in diagnostic assays for ErbB2 protein, e.g., detecting its expression in specific cells, tissues, or serum.

For diagnostic applications, the antibody typically will be labeled with a detectable moiety. Numerous labels are available which can be generally grouped into the following categories;

(a) Radioisotopes, such as $^{35}S$, $^{14}C$, $^{125}I$, $^{3}H$, and $^{131}I$ The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-ErbB2 antibody need not be labeled, and the presence thereof can be detected using a labeled antibody which binds to the ErbB2 antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147–158 (CRC Press, Inc. 1987).

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography. As a matter of convenience, the antibodies of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

VIII. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

EXAMPLE 1

Production and Characterization of Monoclonal Antibody 2C4

The murine monoclonal antibodies 2C4, 7F3 and 4D5 which specifically bind the extracellular domain of ErbB2 were produced as described in Fendly et al., *Cancer Research* 50:1550–1558 (1990). Briefly, NIH 3T3/HER2-3$_{400}$ cells (expressing approximately 1×10 ErbB2 molecules/cell) produced as described in Hudziak et al *Proc. Natl. Acad. Sci.* (USA) 84:7158–7163 (1987) were harvested with phosphate buffered saline (PBS) containing 25 mM EDTA and used to immunize BALB/c mice. The mice were given injections i.p. of $10^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653.

Hybridoma supernatants were screened for ErbB2-binding by ELISA and radioimmunoprecipitation.

The ErbB2 epitopes bound by monoclonal antibodies 4D5, 7F3 and 2C4 were determined by competitive binding analysis (Fendly et al. *Cancer Research* 50:1550–1558 (1990)). Cross-blocking studies were done on antibodies by direct fluorescence on intact cells using the PANDEX™ Screen Machine to quantitate fluorescence. Each monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W. J. Freeman Co. (1980)). Confluent monolayers of NTH 3T3/HER2-$3_{400}$ cells were trypsinized, washed once, and resuspended at $1.75 \times 10^6$ cell/ml in cold PBS containing 0.5% bovine serum albumin (BSA) and 0.1% $NaN_3$. A final concentration of 1% latex particles (IDC, Portland, Oreg.) was added to reduce clogging of the PANDEX™ plate membranes. Cells in suspension, 20 µl, and 20 µl of purified monoclonal antibodies (100 µg/ml to 0.1 µg/ml) were added to the PANDEX™ plate wells and incubated on ice for 30 minutes. A predetermined dilution of FITC-labeled monoclonal antibodies in 20 µl was added to each well, incubated for 30 minutes, washed, and the fluorescence was quantitated by the PANDEX™. Monoclonal antibodies were considered to share an epitope if each blocked binding of the other by 50% or greater in comparison to an irrelevant monoclonal antibody control. In this experiment, monoclonal antibodies 4D5, 7F3 and 2C4 were assigned epitopes 1, G/F and F, respectively.

The growth inhibitory characteristics of monoclonal antibodies 2C4, 7F3 and 4D5 were evaluated using the breast tumor cell line, SK-BR-3 (see Hudziak et al. *Molec. Cell. Biol.* 9(3):1165–1172 (1989)). Briefly, SK-BR-3 cells were detached by using 0.25% (vol/vol) trypsin and suspended in complete medium at a density of $4 \times 10^5$ cells per ml. Aliquots of 100 µl ($4 \times 10^4$ cells) were plated into 96-well microdilution plates, the cells were allowed to adhere, and 100 µl of media alone or media containing monoclonal antibody (final concentration 51g/ml) was then added. After 72 hours, plates were washed twice with PBS (pH 7.5), stained with crystal violet (0.5% in methanol), and analyzed for relative cell proliferation as described in Sugarman et al. *Science* 230:943–945 (1985). Monoclonal antibodies 2C4 and 7F3 inhibited SK-BR-3 relative cell proliferation by about 20% and about 38%, respectively, compared to about 56% inhibition achieved with monoclonal antibody 4D5.

Monoclonal antibodies 2C4, 4D5 and 7F3 were evaluated for their ability to inhibit HRG-stimulated tyrosine phosphorylation of proteins in the $M_r$ 180,000 range from whole-cell lysates of MCF7 cells (Lewis et al. *Cancer Research* 56:1457–1465 (1996)). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis.

However, these cells are ideal for HRG tyrosine phosphorylation assays because under the assay conditions used, in the absence of exogenously added HRG, they exhibit low to undetectable levels of tyrosine phosphorylation proteins in the $M_r$ 180,000 range.

MCF7 cells were plated in 24-well plates and monoclonal antibodies to ErbB2 were added to each well and incubated for 30 minutes at room temperature; then rHRG$\beta 1_{177-244}$ was added to each well to a final concentration of 0.2 nM, and the incubation was continued for 8 minutes. Media was carefully aspirated from each well, and reactions were stopped by the addition of 100 µl of SDS sample buffer (5% SDS, 25 mM DTT, and 25 mM Tris-HCl, pH 6.8). Each sample (25 µl) was electrophoresed on a 4–12% gradient gel (Novex) and then electrophoretically transferred to polyvinylidene difluoride membrane. Antiphosphotyrosine (4G10, from UBI, used at 1 µg/ml) immunoblots were developed, and the intensity of the predominant reactive band at $M_r$-180,000 was quantified by reflectance densitometry, as described previously (Holmes et al. *Science* 256:1205–1210 (1992); Sliwkowski et al. *J. Biol. Chem.* 269:14661–14665 (1994)).

Figure 2A:
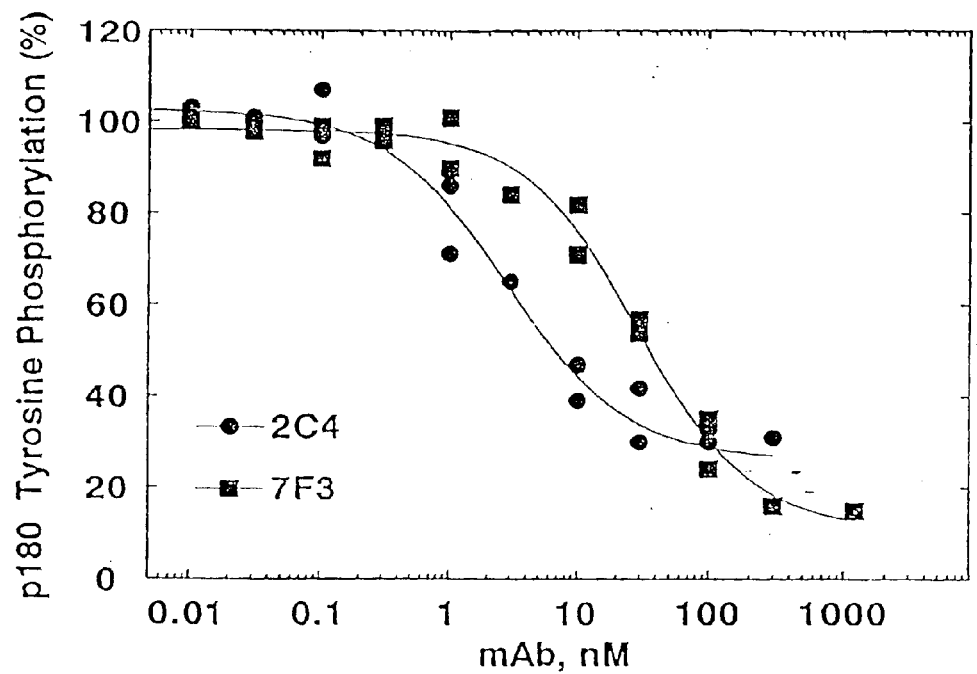
FIGS. 2A and 2B show the effect of anti-ErbB2 monoclonal antibodies 2C4 and 7F3 on rHRGβ1 activation of MCF7 cells.

Monoclonal antibodies 2C4, 7F3, and 4D5, significantly inhibited the generation of a HRG-induced tyrosine phosphorylation signal at $M_r$ 180,000. In the absence of HRG, none of these antibodies were able to stimulate tyrosine phosphorylation of proteins in the $M_r$ 180,000 range. Also, these antibodies do not cross-react with EGFR (Fendly et al. *Cancer Research* 50:1550–1558 (1990)), ErbB3, or ErbB4. Antibodies 2C4 and 7F3 significantly inhibited HRG stimulation of p180 tyrosine phosphorylation to <25% of control. Monoclonal antibody 4D5 was able to block HRG stimulation of tyrosine phosphorylation by ~50%. FIG. 2A shows dose-response curves for 2C4 or 7F3 inhibition of HRG stimulation of p180 tyrosine phosphorylation as determined by reflectance densitometry. Evaluation of these inhibition curves using a 4-parameter fit yielded an $IC_{50}$ of 2.8±0.7 nM and 29.0±4.1 nM for 2C4 and 7F3, respectively.

Figure 2B:
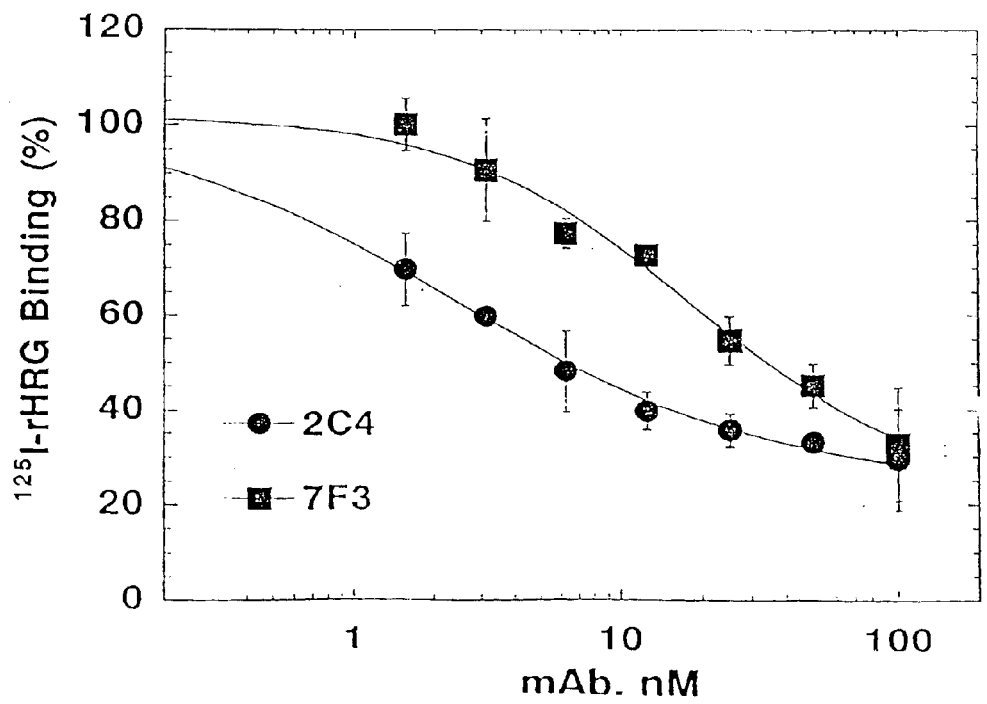

Inhibition of HRG binding to MCF7 breast tumor cell lines by anti-ErbB2 antibodies was performed with monolayer cultures on ice in a 24-well-plate format (Lewis et al. *Cancer Research* 56:1457–1465 (1996)). Anti-ErbB2 monoclonal antibodies were added to each well and incubated for 30 minutes. $^{125}$I-labeled rHRG$\beta 1_{177-224}$ (25 pm) was added, and the incubation was continued for 4 to 16 hours. FIG. 2B provides dose-response curves for 2C4 or 7F3 inhibition of HRG binding to MCF7 cells. Varying concentrations of 2C4 or 7F3 were incubated with MCF7 cells in the presence of 125I-labeled rHRG$\beta 1$, and the inhibition curves are shown in FIG. 2B. Analysis of these data yielded an $IC_{50}$ of 2.4±0.3 nM and 19.0±7.3 nM for 2C4 and 7F3, respectively. A maximum inhibition of -74% for 2C4 and 7F3 were in agreement with the tyrosine phosphorylation data.

Figure 3:
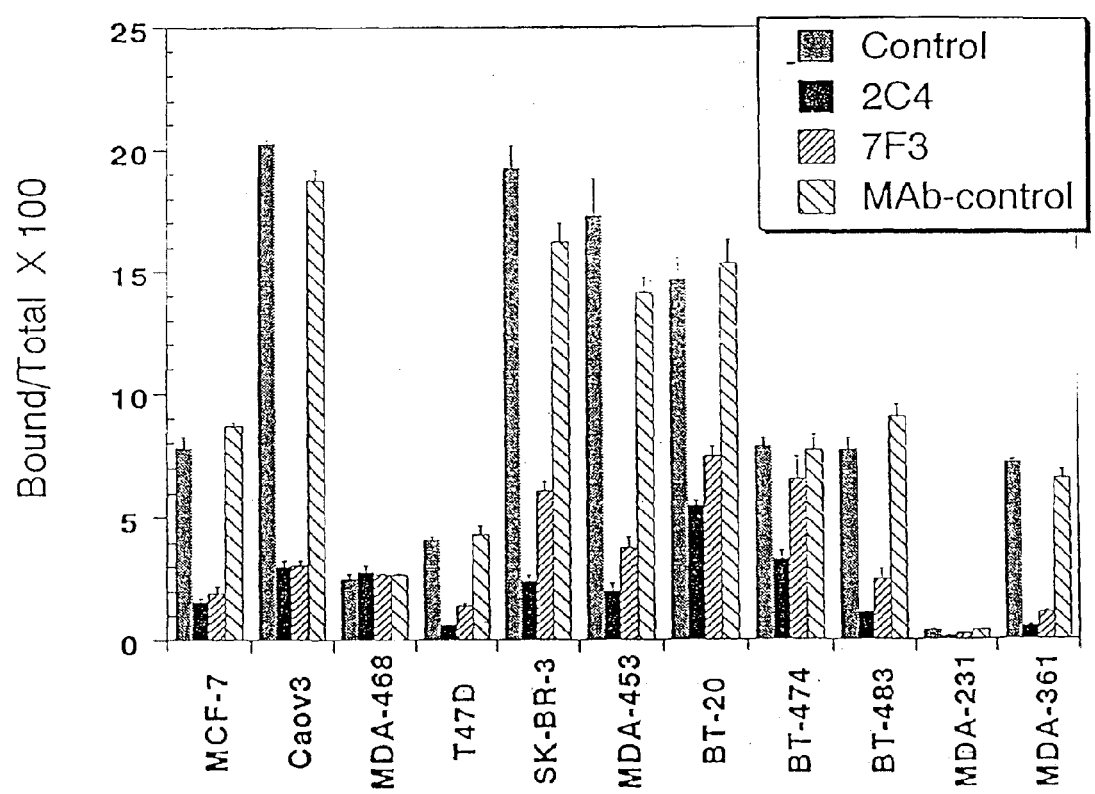
FIG. 3 depicts inhibition of specific $^{125}$I-labeled rHRGβ1$_{177-244}$ binding to a panel of human tumor cell lines by the anti-ErbB2 monoclonal antibodies 2C4 or 7F3. Monoclonal antibody-controls are isotype-matched murine monoclonal antibodies that do not block rHRG binding. Nonspecific $^{125}$I-labeled rHRβ1$_{1177-244}$ binding was determined from parallel incubations performed in the presence of 100 nM rHRGβ1. Values for nonspecific $^{125}$I-labeled rHRGβ1$_{177-244}$ binding were less than 1% of the total for all the cell lines tested.

To determine whether the effect of the anti-ErbB2 antibodies observed on MCF7 cells was a general phenomenon, human tumor cell lines were incubated with 2C4 or 7F3 and the degree of specific $^{125}$I-labeled rHRG$\beta 1$ binding was determined (Lewis et al. *Cancer Research* 56:1457-1465 (1996)). The results from this study are shown in FIG. 3. Binding of $^{121}$I-labeled rHRG$\beta 1$ could be significantly inhibited by either 2C4 or 7F3 in all cell lines, with the exception of the breast cancer cell line MDA-MB-468, which has been reported to express little or no ErbB2. The remaining cell lines are reported to express ErbB2, with the level of ErbB2 expression varying widely among these cell lines. In fact, the range of ErbB2 expression in the cell lines tested varies by more than 2 orders of magnitude. For example, BT-20, MCF7, and Caov3 express $-10^4$ ErbB2 receptors/cell, whereas BT474 and SK-BR-3 express $-10^6$ ErbB2 receptors/cell. Given the wide range of ErbB2 expression in these cells and the data above, it was concluded that the interaction between ErbB2 and ErbB3 or ErbB4, was itself a high-affinity interaction that takes place on the surface of the plasma membrane.

Figure 4A:
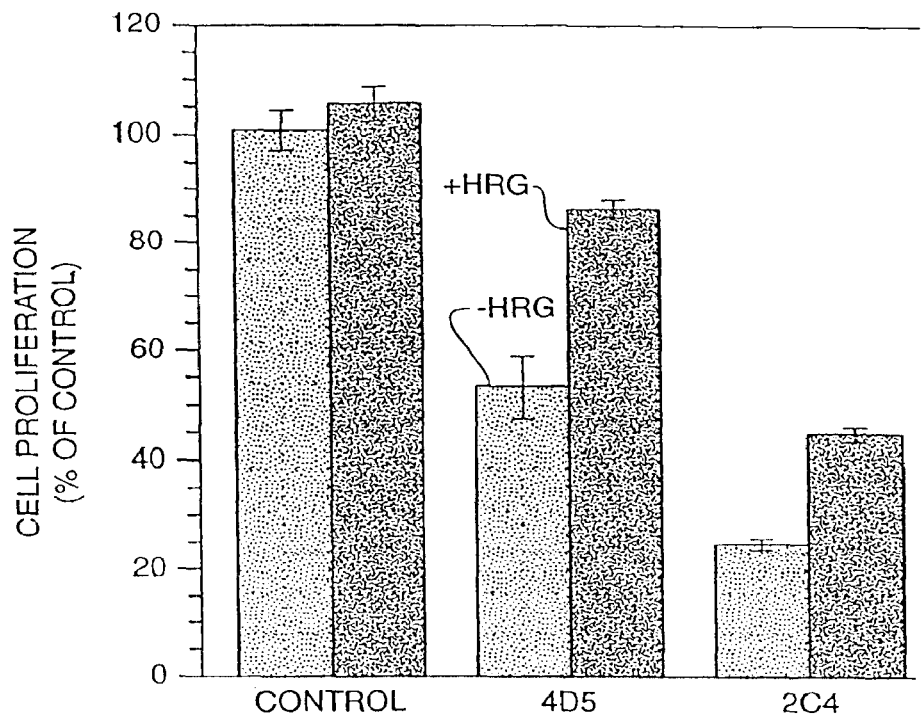
FIGS. 4A and 4B show the effect of monoclonal antibodies 2C4 and 4D5 on proliferation of MDA-MB-175 (FIG. 4A) and SK-BR-3 (FIG. 4B) cells. MDA-MB-175 and SK-BR-3 cells were seeded in 96 well plates and allowed to adhere for 2 hours. Experiment was carried out in medium containing 1% serum. Anti-ErbB2 antibodies or medium alone were added and the cells were incubated for 2 hours at 37° C. Subsequently rHRGβ1(1 nM) or medium alone were added and the cells were incubated for 4 days. Monolayers were washed and stained/fixed with 0.5% crystal violet. To determine cell proliferation the absorbance was measured at 540 nm.
Figure 4B:
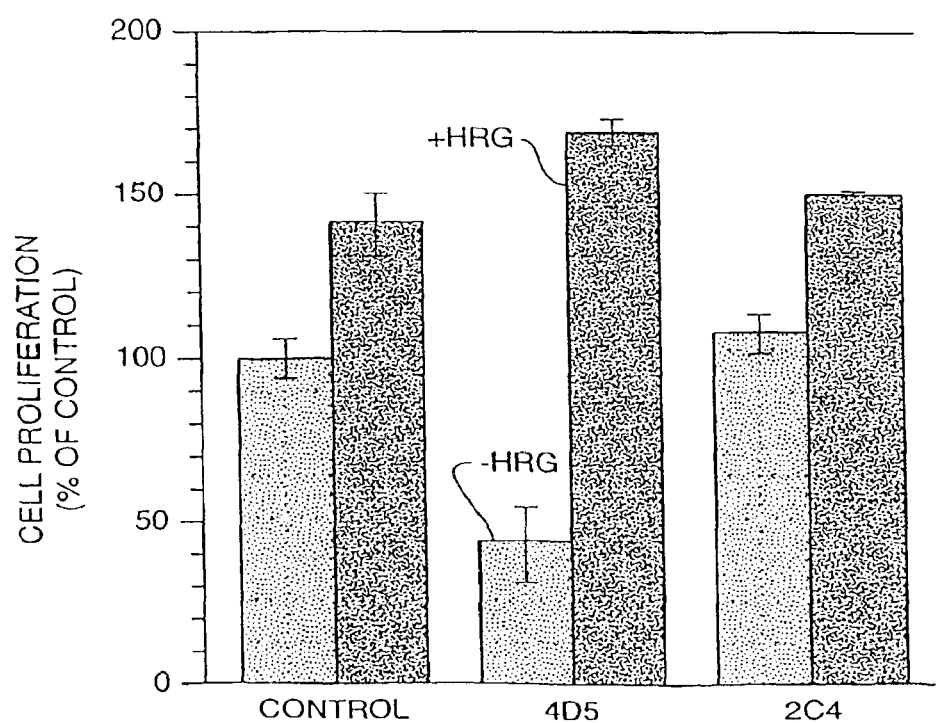

The growth inhibitory effects of monoclonal antibodies 2C4 and 4D5 on MDA-MB-175 and SK-BR-3 cells in the presence or absence of exogenous rHRG$\beta 1$ was assessed (Schaefer et al. *Oncogene* 15:1385–1394 (1997)). ErbB2 levels in MDA-MB-175 cells are 4–6 times higher than the level found in normal breast epithelial cells and the ErbB2–ErbB4 receptor is constitutively tyrosine phosphorylated in MDA-MB-175 cells. MDA-MB-175 cells were treated with an anti-ErbB2 monoclonal antibodies 2C4 and 4D5 (10 µg/mL) for 4 days. In a crystal violet staining assay, incubation with 2C4 showed a strong growth inhibitory effect on this cell line (FIG. 4A). Exogenous HRG did not significantly reverse this inhibition. On the other hand 2C4 revealed no inhibitory effect on the ErbB2 overexpressing cell line SK-BR-3 (FIG. 4B). Monoclonal antibody 2C4 was able to inhibit cell proliferation of MDA-MB-175 cells to a greater extent than monoclonal antibody 4D5, both in the presence and absence of exogenous HRG. Inhibition of cell proliferation by 4D5 is dependent on the ErbB2 expression level (Lewis et al. *Cancer Immunol. Immunother.* 37:255–263 (1993)). A maximum inhibition of 66% in SK-BR-3 cells could be detected (FIG. 4B). However this effect could be overcome by exogenous HRG.

EXAMPLE 2

HRG Dependent Association of ErbB2 with ErbB3 is Blocked by Monoclonal Antibody 2C4

The ability of ErbB3 to associate with ErbB2 was tested in a co-immunoprecipitation experiment. $1.0 \times 10^6$ MCF7 or SK-BR-3 cells were seeded in six well tissue culture plates in 50:50 DMEM/Ham's F12 medium containing 10% fetal bovine serum (FBS) and 10 mM HEPES, pH 7.2 (growth medium), and allowed to attach overnight. The cells were starved for two hours in growth medium without serum prior to beginning the experiment The cells were washed briefly with phosphate buffered saline (PBS) and then incubated with either 100 nM of the indicated antibody diluted in 0.2% w/v bovine serum albumin (BSA), RPMI medium, with 10 mM HEPES, pH 7.2 (binding buffer), or with binding buffer alone (control). After one hour at room temperature, HRG was added to a final concentration of 5 nM to half the wells (+). A similar volume of binding buffer was added to the other wells (−). The incubation was continued for approximately 10 minutes.

Supernatants were removed by aspiration and the cells were lysed in RPMI, 10 mM HEPES, pH 7.2, 1.0% v/v TRITON X-100™, 1.0% w/v CHAPS (lysis buffer), containing 0.2 mM PMSF, 10 µg/ml leupeptin, and 10 TU/ml aprotinin. The lysates were cleared of insoluble material by centrifugation.

ErbB2 was immunoprecipitated using a monoclonal antibody covalently coupled to an affinity gel (Affi-Prep 10, Bio-Rad). This antibody (Ab-3, Oncogene Sciences) recognizes a cytoplasmic domain epitope. Immunoprecipitation was performed by adding 10 µl of gel slurry containing approximately 8.5 µg of immobilized antibody to each lysate, and the samples were allowed to mix at room temperature for two hours. The gels were then collected by centrifugation. The gels were washed batchwise three times with lysis buffer to remove unbound material. SDS sample buffer was then added and the samples were heated briefly in a boiling water bath.

Supernatants were run on 4–12% polyacrylamide gels and electroblotted onto nitrocellulose membranes. The presence of ErbB3 was assessed by probing the blots with a polyclonal antibody against a cytoplasmic domain epitope thereof (c-17, Santa Cruz Biotech). The blots were visualized using a chemiluminescent substrate (ECL, Amersham).

As shown in the control lanes of FIGS. 5A and 5B, for MCF7 and SK-BR-3 cells, respectively, ErbB3 was present in an ErbB2 immunoprecipitate only when the cells were stimulated with HRG. If the cells were first incubated with monoclonal antibody 2C4, the ErbB3 signal was abolished in MCF7 cells (FIG. 5A, lane 2C4+) or substantially reduced in SK-BR-3 cells (FIG. 5B, lane 2C4+). As shown in FIGS. 5A–B, monoclonal antibody 2C4 blocks heregulin dependent association of ErbB3 with ErbB2 in both MCF7 and SK-BR-3 cells substantially more effectively than HERCEPTIN®. Preincubation with HERCEPTIN® decreased the ErbB3 signal in MCF7 lysates but had little or no effect on the amount of ErbB3 co-precipitated from SK-BR-3 lysates. Preincubation with an antibody against the EGF receptor (Ab-1, Oncogene Sciences) had no effect on the ability of ErbB3 to co-immunoprecipitate with ErbB2 in either cell line.

EXAMPLE 3

Humanized 2C4 Antibodies

The variable domains of murine monoclonal antibody 2C4 were first cloned into a vector which allows production of a mouse/human chimeric Fab fragment. Total RNA was isolated from the hybridoma cells using a Stratagene RNA extraction kit following manufacturer's protocols. The variable domains were amplified by RT-PCR, gel purified, and inserted into a derivative of a pUC119-based plasmid containing a human kappa constant domain and human $C_H1$ domain as previously described (Carter et al. *PNAS* (USA) 89:4285 (1992); and U.S. Pat. No. 5,821,337). The resultant plasmid was transformed into *E. coli* strain 16C9 for expression of the Fab fragment. Growth of cultures, induction of protein expression, and purification of Fab fragment were as previously described (Werther et al. *J. Immunol.* 157:4986–4995 (1996); Presta et al. *Cancer Research* 57:4593–4599 (1997)).

Figure 6A:
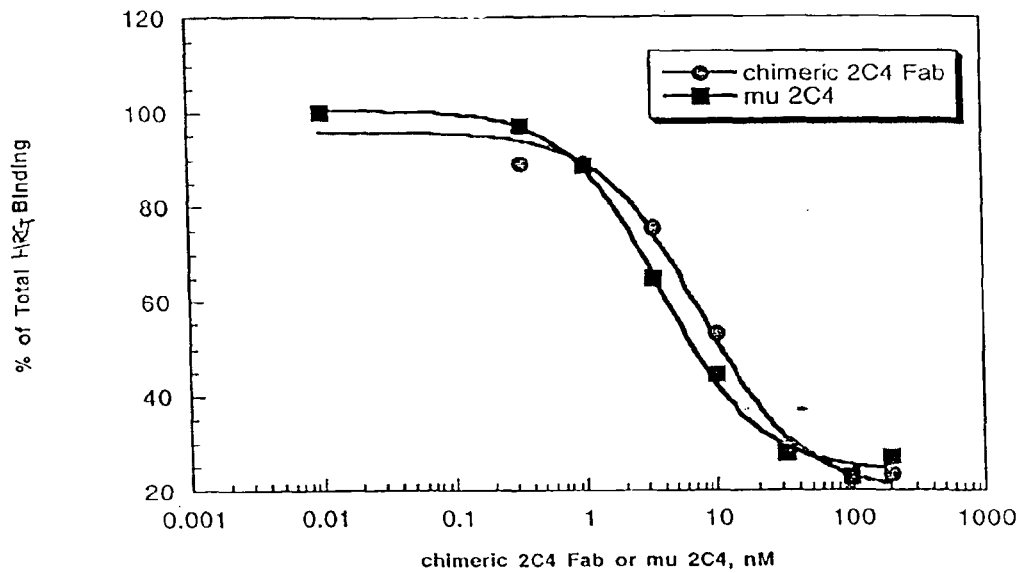
FIGS. 6A and 6B compare the activities of intact murine monoclonal antibody 2C4 (mu 2C4) and a chimeric 2C4 Fab fragment.
Figure 6B:
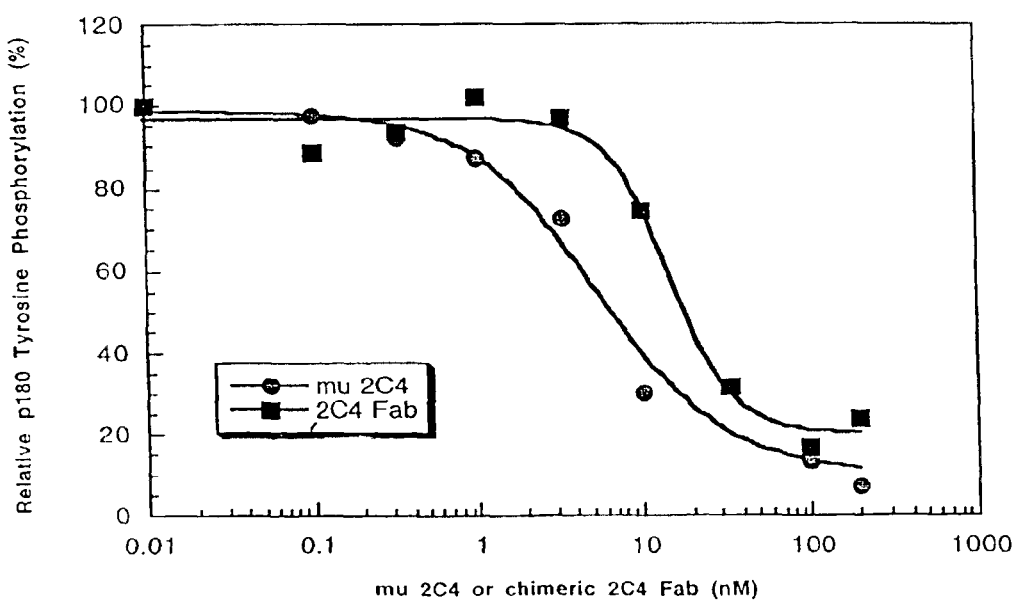

Purified chimeric 2C4 Fab fragment was compared to the murine parent antibody 2C4 with respect to its ability to inhibit $^{125}$I-HRG binding to MCF7 cells and inhibit rHRG activation of p180 tyrosine phosphorylation in MCF7 cells. As shown in FIG. 6A, the chimeric 2C4 Fab fragment is very effective in disrupting the formation of the high affinity ErbB2–ErbB3 binding site on the human breast cancer cell line, MCF7. The relative $IC_{50}$ value calculated for intact murine 2C4 is 4.0±0.4 nM, whereas the value for the Fab fragment is 7.7±1.1 nM. As illustrated in FIG. 6B, the monovalent chimeric 2C4 Fab fragment is very effective in disrupting HRG-dependent ErbB2–ErbB3 activation. The $IC_{50}$ value calculated for intact murine monoclonal antibody 2C4 is 6.0±2 nM, whereas the value for the Fab fragment is 15.0 t 2 nM.

Figure 8A:
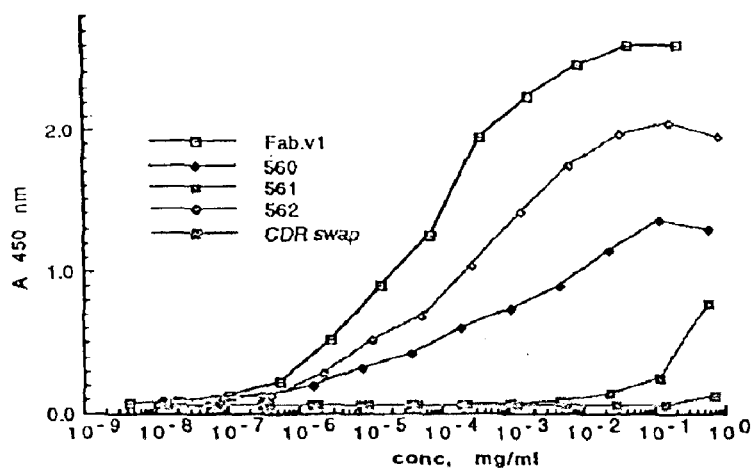
FIGS. 8A to C show binding of chimeric Fab 2C4 (Fab.v1) and several humanized 2C4 variants to ErbB2 extracellular domain (ECD) as determined by ELISA in Example 3.

DNA sequencing of the chimeric clone allowed identification of the CDR residues (Kabat et al, *Sequences of Proteins of Immunological Interest*, 5$^{th}$ Ed. Public Health Service, National Institutes of Health, Bethesda, Md. (1991)) (FIGS. 7A and B). Using oligonucleotide site-directed mutagenesis, all six of these CDR regions were introduced into a complete human framework ($V_L$ kappa subgroup I and $V_H$ subgroup III) contained on plasmid VX4 as previously described (Presta et al., *Cancer Research* 57: 4593–4599 (1997)). Protein from the resultant "CDR-swap" was expressed and purified as above. Binding studies were performed to compare the two versions. Briefly, a NUNC MAXISORP™ plate was coated with 1 microgram per ml of ErbB2 extracellular domain (ECD; produced as described in WO 90/14357) in 50 mM carbonate buffer, pH 9.6, overnight at 4° C., and then blocked with ELISA diluent (0.5% BSA, 0.05% polysorbate 20, PBS) at room temperature for 1 hour. Serial dilutions of samples in ELISA diluent were incubated on the plates for 2 hours. After washing, bound Fab fragment was detected with biotinylated murine anti-human kappa antibody (ICN 634771) followed by streptavidin-conjugated horseradish peruxidase (Sigma) and using 3,3',5,5'-tetramethyl benzidine (Kirkegaard & Perry Laboratories, Gaithersburg, Md.) as substrate. Absorbance was read at 450 nm. As shown in FIG. 8A, all binding was lost on construction of the CDR-swap human Fab fragment.

Figure 9:
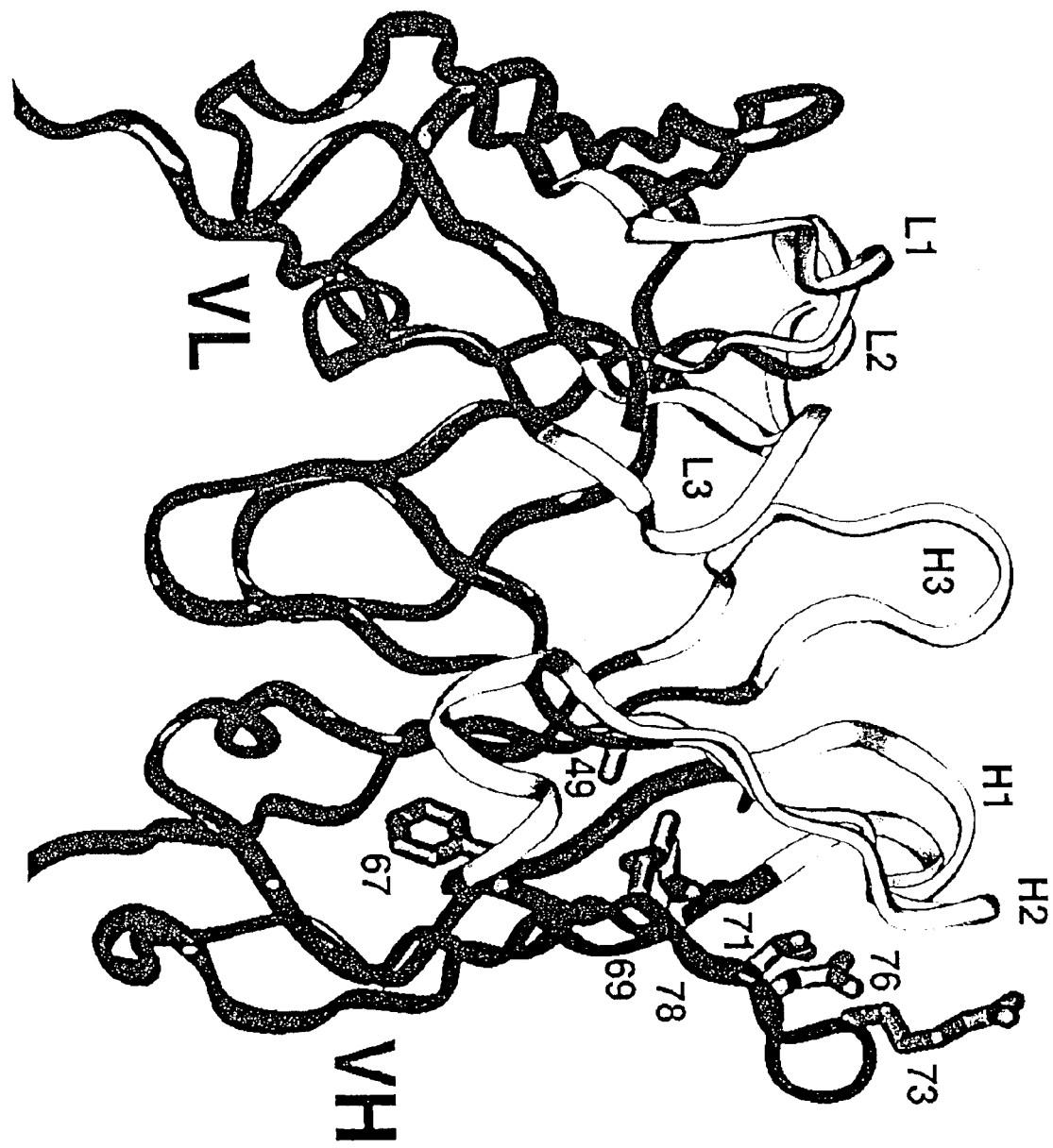
FIG. 9 is a ribbon diagram of the $V_L$ and $V_H$ domains of monoclonal antibody 2C4 with white CDR backbone labeled (L1, L2, L3, H1, H2, H3). $V_H$ sidechains evaluated by mutagenesis during humanization (see Example 3, Table 2) are also shown.

To restore binding of the humanized Fab, mutants were constructed using DNA from the CDR-swap as template. Using a computer generated model (FIG. 9), these mutations were designed to change human framework region residues to their murine counterparts at positions where the change might affect CDR conformations or the antibody-antigen interface. Mutants are shown in Table 2.

TABLE 2

Designation of Humanized 2C4 FR Mutations

| Mutant no. | Framework region (FR) substitutions |
|---|---|
| 560 | ArgH71Val |
| 561 | AspH73Arg |
| 562 | ArgH71Val, AspH73Arg |
| 568 | ArgH71Val, AspH73Arg, AlaH49Gly |
| 569 | ArgH71Val, AspH73Arg, PheH67Ala |
| 570 | ArgH71Val, AspH73Arg, AsnH76Arg |
| 571 | ArgH71Val, AspH73Arg, LeuH78Val |
| 574 | ArgH71Val, AspH73Arg, IleH69Leu |
| 56869 | ArgH71Val, AspH73Arg, AlaH49Gly, PheH67Ala |

Figure 8B:
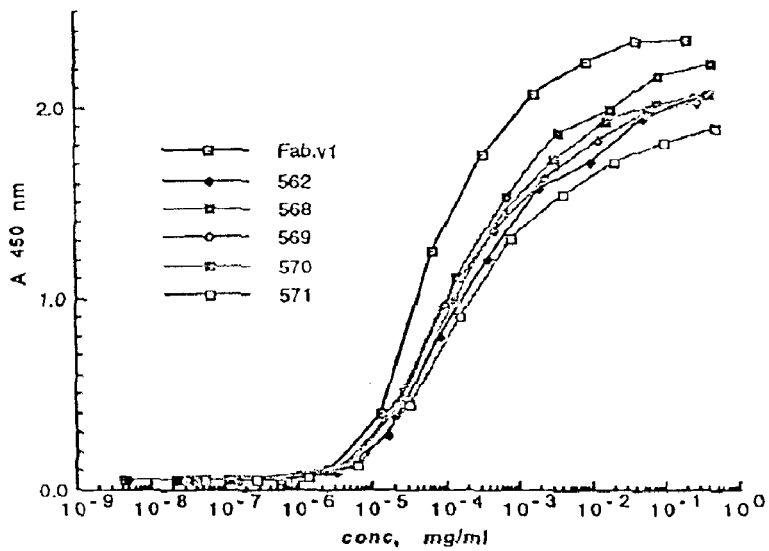
Figure 8C:
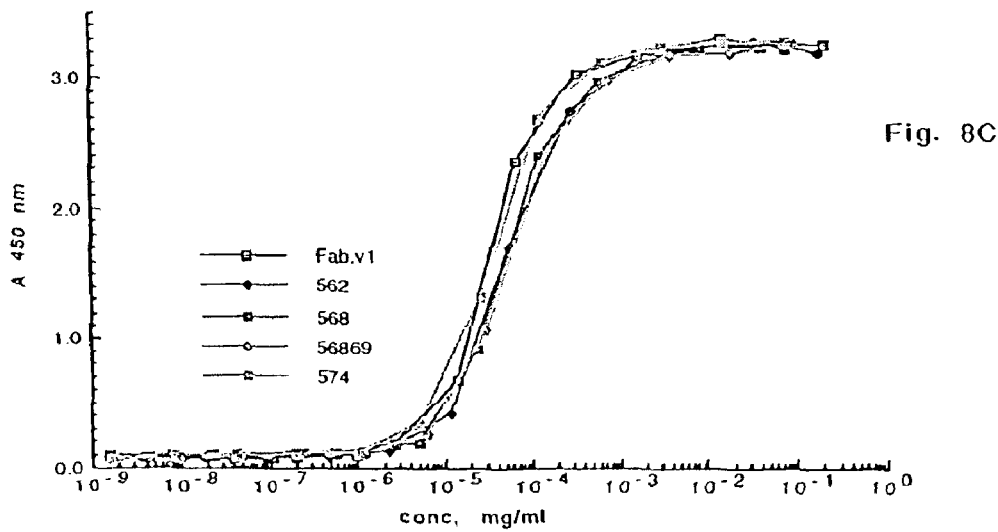

Binding curves for the various mutants are shown in FIGS. 8A–C. Humanized Fab version 574, with the changes ArgH71Val, AspH73Arg and IleH69Leu, appears to have binding restored to that of the original chimeric 2C4 Fab fragment. Additional FR and/or CDR residues, such as L2, L54, L55, L56, H35 and/or H48, may be modified (e.g. substituted as follows—IleL2Thr; ArgL54Leu; TyrL55Glu; ThrL56Ser; AspH35Ser; and ValH48Ile) in order to further refine or enhance binding of the humanized antibody. Alternatively, or additionally, the humanized antibody may be affinity matured (see above) in order to further improve or refine its affinity and/or other biological activities.

Humanized 2C4 version 574 was affinity matured using a phage-display method. Briefly, humanized 2C4.574 Fab was cloned into a phage display vector as a geneIII fusion. When phage particles are induced by infection with M13KO7 helper phage, this fusion allows the Fab to be displayed on the N-terminus of the phage tail-fiber protein, geneIII (Baca et al. *J Biol Chem.* 272:10678 (1997)).

Individual libraries were constructed for each of the 6 CDRs identified above. In these libraries, the amino acids in the CDRs which were identified using a computer generated model (FIG. 9) as being potentially significant in binding to ErbB2 were randomized using oligos containing "NNS" as their codons. The libraries were then panned against ErbB2 ECD coated on NUNC MAXISORP™ plates with 3% dry milk in PBS with 0.2% TWEEN 20® (MPBST) used in place of all blocking solutions. In order to select for phage with affinities higher than that of 2C4.574, in panning rounds 3, 4, and 5, soluble ErbB2 ECD or soluble Fab 2C4.574 was added during the wash steps as competitor. Wash times were extended to 1 hour at room temperature.

After 5 rounds of panning, individual clones were again analyzed by phage-ELISA. Individual clones were grown in Costar 96-well U-bottomed tissue culture plates, and phage were induced by addition of helper phage. After overnight growth, *E. coli* cells were pelleted, and the phage-containing supernates were transferred to 96-well plates where the phage were blocked with MPBST for 1 hr at room temperature. NUNC MAXISORP™ plates coated with ErbB2 ECD were also blocked with MPBST as above. Blocked phage were incubated on the plates for 2 hours. After washing, bound phage were detected using horseradish-peroxidase-conjugated anti-M 13 monoclonal antibody (Amersham Pharmacia Biotech, Inc. 27-9421-01) diluted 1:5000 in MPBST, followed by 3,3',5,5',-tetramethyl benzidine as substrate. Absorbance was read at 450 nm.

The 48 clones from each library which gave the highest signals were DNA sequenced. Those clones whose sequences occurred the most frequently were subcloned into the vector described above which allows expression of soluble Fabs. These Fabs were induced, proteins purified and the purified Fabs were analyzed for binding by ELISA as described above and the binding was compared to that of the starting humanized 2C4.574 version.

After interesting mutations in individual CDRs were identified, additional mutants which were various combinations of these were constructed and tested as above. Mutants which gave improved binding relative to 574 are described in Table 3.

TABLE 3

Designation of mutants derived from affinity maturation of 2C4.574

| Mutant Name | Change from 574 | Mutant/574* |
|---|---|---|
| H3.A1 | serH99trp, metH34leu | 0.380 |
| L2.F5 | serL50trp, tyrL53gly, metH34leu | 0.087 |
| H1.3.B3 | thrH28gln, thrH30ser, metH34leu | 0.572 |
| L3.G6 | tyrL92pro, ileL93lys, metH34leu | 0.569 |
| L3.G11 | tyrL92ser, ileL93arg, tyrL94gly, metH34leu | 0.561 |
| L3.29 | tyrL92phe, tyrL96asn, metH34leu | 0.552 |
| L3.36 | tyrL92phe, tyrL94leu, tyrL96pro, metH34leu | 0.215 |
| 654 | serL50trp, metH34leu | 0.176 |
| 655 | metH34ser | 0.542 |
| 659 | serL50trp, metH34ser | 0.076 |
| L2.F5.H3.A1 | serL50trp, tyrL53gly, metH34leu, serH99trp | 0.175 |
| L3G6.H3.A1 | tyrL92pro, ileL93lys, metH34leu, serH99trp | 0.218 |
| H1.3.B3.H3.A1 | thrH28gln, thrH30ser, metH34leu, serH99trp | 0.306 |
| L3.G11.H3.A1 | tyrL92ser, ileL93arg, tyrL94gly, metH34leu, serH99trp | 0.248 |
| 654.H3.A1 | serL50trp, metH34leu, serH99trp | 0.133 |
| 654.L3.G6 | serL50trp, metH34leu, tyrL92pro, ileL93lys | 0.213 |
| 654.L3.29 | serL50trp, metH34leu, tyrL92phe, tyrL96asn | 0.236 |
| 654.L3.36 | serL50trp, metH35leu, tyrL92phe, tyrL94leu, tyrL96pro | 0.141 |

*Ratio of the amount of mutant needed to give the mid-OD of the standard curve to the amount of 574 needed to give the mid-OD of the standard curve in an Erb2-ECD ELISA. A number less than 1.0 indicates that the mutant binds Erb2 better than 574 binds.

The following mutants have also been constructed, and are currently under evaluation:

| | |
|---|---|
| 659.L3.G6 | serL50trp, metH34ser, tyrL92pro, ileL93lys |
| 659.L3.G11 | serL50trp, metH34ser, tyrL92ser, ileL93arg, tyrL94gly |
| 659.L3.29 | serL50trp, metH34ser, tyrL92phe, tyrL96asn |
| 659.L3.36 | serL50trp, metH34ser, tyrL92phe, tyrL94leu, tyrL96pro |
| L2F5.L3.G6 | serL50trp, tyrL53gly, metH34leu, tyrL92pro, ileL93lys |
| L2F5.L3G11 | serL50trp, tyrL53gly, metH34leu, tyrL92ser, ileL93arg, tyrL94gly |

| | -continued | |
|---|---|---|
| L2F5.L29 | serL50trp, tyrL53gly, metH34leu, tyrL92phe, tyrL96asn | |
| L2F5.L36 | serL50trp, tyrL53gly, metH34leu, tyrL92phe, tyrL94leu, tyrL96pro | |
| L2F5.L3G6.655 | serL50trp, tyrL53gly, metH35ser, tyrL92pro, ileL93lys | |
| L2F5.L3G11.655 | serL50trp, tyrL53gly, metH34ser, tyrL92ser, ileL93arg, tyrL94gly | |
| L2F5.L29.655 | serL50trp, tyrL53gly, metH34ser, tyrL92phe, tyrL96asn | |
| L2F5.L36.655 | serL50trp, tyrL53gly, metH34ser, tyrL92phe, tyrL94leu, tyrL96pro | |

The following mutants, suggested by a homology scan, are currently being constructed:

| 678 | thrH30ala |
|---|---|
| 679 | thrH30ser |
| 680 | lysH64arg |
| 681 | leuH96val |
| 682 | thrL97ala |
| 683 | thrL97ser |
| 684 | tyrL96phe |
| 685 | tyrL96ala |
| 686 | tyrL91phe |
| 687 | thrL56ala |
| 688 | glnL28ala |
| 689 | glnL28glu |

The preferred amino acid at H34 would be methionine. A change to leucine might be made if there were found to be oxidation at this position.

AsnH52 and asnH53 were found to be strongly preferred for binding. Changing these residues to alanine or aspartic acid dramatically decreased binding.

An intact antibody comprising the variable light and heavy domains of humanized version 574 with a human IgG1 heavy chain constant region has been prepared (see U.S. Pat. No. 5,821,337). The intact antibody is produced by Chinese Hamster Ovary (CHO) cells. That molecule is designated rhuMAb 2C4 herein.

EXAMPLE 4

Monoclonal Antibody 2C4 Blocks EGF, TGF-α or HRG Mediated Activation of MAPK

Many growth factor receptors signal through the mitogen-activated protein kinase (MAPK) pathway. These dual specificity kinases are one of the key endpoints in signal transduction pathways that ultimately triggers cancer cells to divide. The ability of monoclonal antibody 2C4 or HERCEPTIN® to inhibit EGF, TGF-α or HRG activation of MAPK was assessed in the following way.

MCF7 cells ($10^5$ cells/well) were plated in serum containing media in 12-well cell culture plates. The next day, the cell media was removed and fresh media containing 0.1% serum was added to each well. This procedure was then repeated the following day and prior to assay the media was replaced with serum-free binding buffer (Jones et al. *J. Biol. Chem.* 273:11667–74(1998); and Schaefer et al. *J. Biol. Chem.* 274:859–66(1999)). Cells were allowed to equilibrate to room temperature and then incubated for 30 minutes with 0.5 mL of 200 nM HERCEPTIN® or monoclonal antibody 2C4. Cells were then treated with 1 nM EGF, 1 nM TGF-α or 0.2 nM HRG for 15 minutes. The reaction was stopped by aspirating the cell medium and then adding 0.2 mL SDS-PAGE sample buffer containing 1% DTT.MAPK activation was assessed by Western blotting using an anti-active MAPK antibody (Promega) as described previously (Jones et al. *J. Biol. Chem.* 273:11667–74 (1998)).

Figure 10:
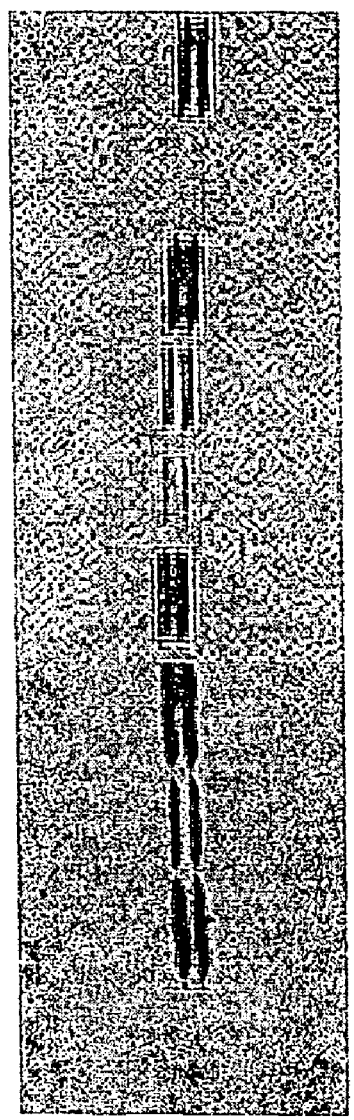
FIG. 10 depicts the effect of monoclonal antibody 2C4 or HERCEPTIN®>on EGF, TGF-α, or HRG-mediated activation of mitogen-activated protein kinase (MAPK).

As shown in FIG. 10, monoclonal antibody 2C4 significantly blocks EGF, TGF-α and HRG mediated activation of MAPK to a greater extent than HERCEPTIN®. These data suggest that monoclonal antibody 2C4 binds to a surface of ErbB2 that is used for its association with either EGFR or ErbB3 and thus prevents the formation of the signaling receptor complex.

Monoclonal antibody 2C4 was also shown to inhibit heregulin (HRG)-dependent Akt activation. Activation of the PI3 kinase signal transduction pathway is important for cell survival (Carraway et al *J. Biol. Chem.* 270:7111–6 (1995)). In tumor cells, PI3 kinase activation may play a role in the invasive phenotype (Tan et al. *Cancer Reearch.* 59: 1620–1625, (1999)). The survival pathway is primarily mediated by the serine/threonine kinase AKT (Bos et al *Trends Biochem Sci.* 20: 441–442 (1995). Complexes formed between ErbB2 and either ErbB3 or EGFR can initiate these pathways in response to heregulin or EGF, respectively (Olayioye et al. *Mol. & Cell. Biol.* 18: 5042–51 (1998); Karunagaran et al., *EMBO Journal.* 15:254–264 (1996); and Krymskaya et al *Am. J. Physiol.* 276: L246–55 (1999)). Incubation of MCF7 breast cancer cells with 2C4 inhibits heregulin-mediated AKT activation. Moreover, the basal level of AKT activation present in the absence of heregulin addition is further reduced by the addition of 2C4. These data suggest that 2C4 may inhibit ErbB ligand-activation of PI3 kinase and that this inhibition may lead to apoptosis. The increased sensitivity to apoptosis may manifest in a greater sensitivity of tumor cells to the toxic effects of chemotherapy.

Thus, monoclonal antibody 2C4 inhibits ligand initiated ErbB signaling through two major signal transduction pathways—MAP Kinase (a major proliferative pathway) and P 13 kinase (a major survival/anti-apoptotic pathway).

EXAMPLE 5

Combination of Monoclonal Antibody 2C4 and HERCEPTIN® in vivo

A xenograft model using the lung adenocarcinoma cell line, Calu-3, was used to assess the efficacy of anti-HER2 monoclonal antibodies, either alone or in combination, to suppress tumor growth. Female NCR nude mice were inoculated subcutaneously with $20 \times 10^6$ cells in 0.1 mL. Tumor measurements were taken twice per week and when tumor nodules reached a volume of 100 mm$^3$, animals were randomized to 7 treatment groups. The treatment groups were:

(a) control monoclonal antibody, MAb 1766;

(b) HERCEPTIN®, 10 mg/kg;

(c) monoclonal antibody 7C2, 10 mg/kg;

(d) monoclonal antibody 2C4, 10 mg/kg;

(e) HERCEPTIN® and 7C2, each at 10 mg/kg;

(f) HERCEPTIN® and 2C4, each at 10 mg/kg; and (g) Monoclonal antibodies 2C4 and 7C2, each at 10 mg/kg.

Animals were treated twice per week until day 24. Tumor volumes were measured twice per week until day 38.

Figure 11:
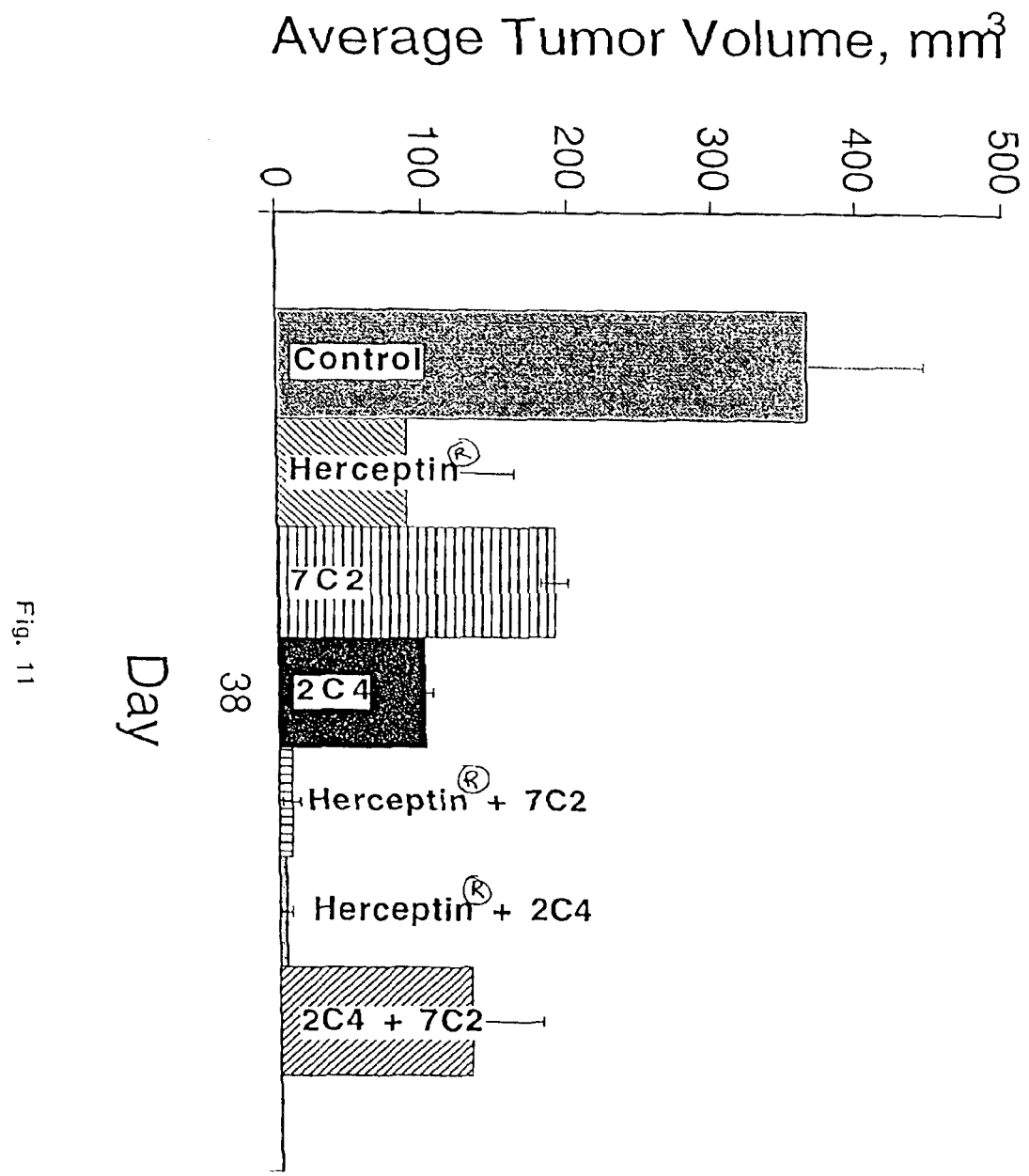
FIG. 11 is a bar graph showing the effect of anti-ErbB2 antibodies (alone or in combinations) on Calu3 lung adenocarcinoma xenografts (3+ErbB2 overexpressor). Note: treatment was stopped on day 24.

As shown in the bar graph in FIG. 11, treatment of the Calu-3 tumor-bearing mice with 2C4 or HERCEPTIN® significantly inhibited the growth of the tumors. The combination of HERCEPTIN®D and 2C4 or HERCEPTIN® and 7C2 was superior to either monoclonal antibody administered alone.

EXAMPLE 6

Treating Colorectal Cancer with Monoclonal Antibody 2C4 Human colorectal cell lines such as HCA-7, LS174T or CaCo-2 are implanted subcutaneously in athymic nude mice as described in Sheng et al. *J. Clin. Invest.* 99:2254–2259 (1997). Once tumors are established to about 100 mm$^3$ in volume, groups of animals are treated with 10–50 mg/kg of monoclonal antibody 2C4 administered twice weekly by injection in the intraperitoneal cavity. Monoclonal antibody 2C4 suppresses growth of colorecial xenografts in vivo.

EXAMPLE 7

Treating Breast Cancer with Humanized 2C4

Figure 12:
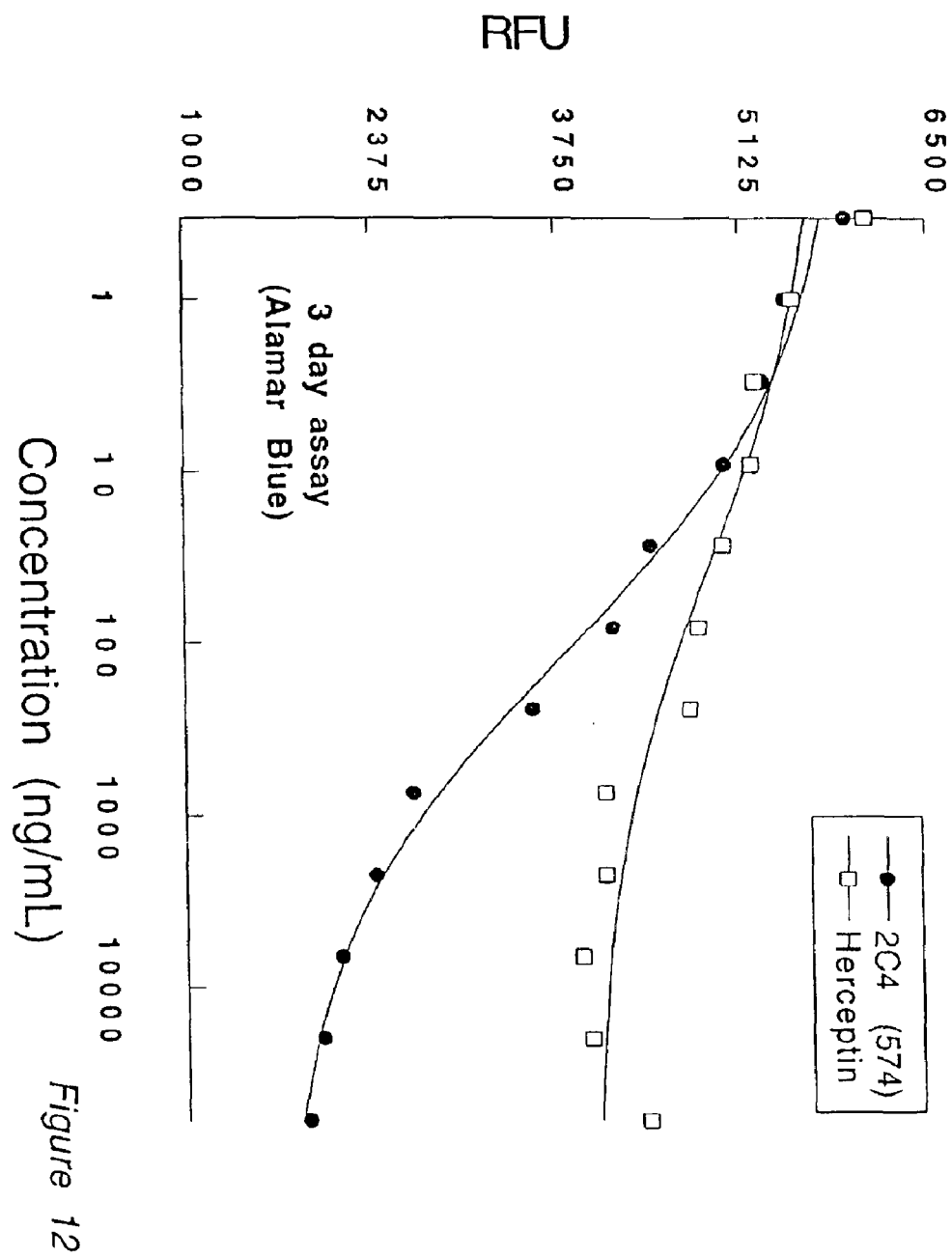
FIG. 12 depicts the effect of recombinant humanized monoclonal antibody 2C4 (rhuMAb 2C4) or HERCEPTIN® on the growth of MDA-175 cells as assessed in an Alamar Blue assay.

The effect of rhuMAb 2C4 or HERCEPTIN® on human breast cancer cells which do not overexpress ErbB2 was assessed in a 3 day Alamar Blue assay (Ahmed, S. A. *J. Immunol. Methods* 170:211–224 (1994); and Page et al. *Int. J. Oncol.* 3:473–476(1994)). The cells used in this assay were MDA-175 human breast cancer cells which express ErbB2 at a 1+level. As shown in FIG. 12, the growth of the breast cancer cell line, MDA-175, is significantly inhibited in a dose-dependent manner by the addition of rhuMAb 2C4 in comparison to HERCEPTIN® treatment.

Figure 13:
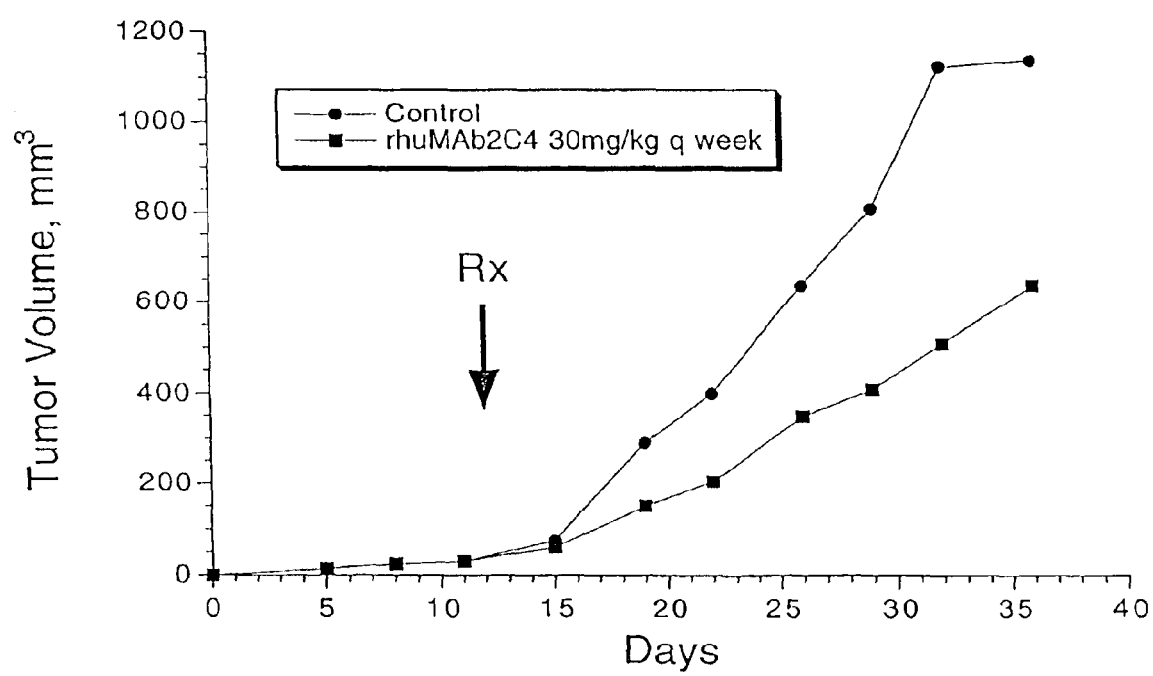
FIG. 13 shows the efficacy of rhuMAb 2C4 against MCF7 xenografts.

The efficacy of rhuMAb 2C4 against MCF7 xenografts which are estrogen receptor positive (ER+) and express low levels of ErbB2 was assessed. Female mice supplemented with estrogen were used. rhuMAb 2C4 was administered at a dose of 30 mg/kg every week. As shown in FIG. 13, rhuMAb 2C4 was effective in inhibiting breast cancer tumor growth in vivo, where the breast cancer was not characterized by overexpression of ErbB2.

EXAMPLE 8

Pharmacokinetics, Metabolism and Toxicology of 2C4 rhuMAb 2C4 was stable in human serum. No evidence or aggregates of complex formation in biological matrices was observed. In mice, rhuMAb2C4 cleared faster than HERCEPTIN®. Pharmacokinetic studies indicate that weekly administration of about 2–6 mg/kg of rhuMAb 2C4 should result in serum concentrations similar to HERCEPTIN®D as presently dosed. Resulting serum 2C4 exposure should greatly exceed IC, determined in vitro.

A toxicology study was carried out in cynomolgus monkeys (2 males and 2 females per group). rhuMab 2C4 was administered intravenously at 0, 10, 50 or 100 mg/kg twice a week for 4 weeks. The toxicology study measurements included body weights (−2, —I weeks and weekly thereafter); food consumption (qualitative, daily); physical examinations with assessment of blood pressure, electrocardiogram (ECG), and body temperature (−2, −1 weeks and weeks 2 and 4, 4 hours post-dose following that weeks second dose); cardiac ultrasound evaluations (following first dose week 1 and end of study, week 4); clinical pathology (baseline and end of weeks 2 and 4); urinalysis (baseline and end of weeks 2 and 4); antibody analysis sampling (baseline and end of weeks 2 and 4); as well as necropsy and histopathology analysis.

All animals in all groups survived to the end of the study. No significant clinical observations, or differences among groups, were noted. Necropsy results showed no significant gross abnormalities in organs from any animals. No significant microscopic abnormalities were observed by in tissues from any of the animals. No significant changes in ECG were noted from initiation to completion of the study. In addition, no differences among the groups were seen.

EXAMPLE 9

Dose Escalation

Cancer patients are administered a first dose of rhuMAb 2C4 at one of five dose levels (0.05, 0.5, 2.0, 4.0 or 10 mg/kg; 6 subjects per dose level), followed by a 4 week wash-out. Week 5 patients are given the same dose weekly 4 times followed by a further 4 week wash-out. Patients with complete response, partial response or stable disease are eligible for extension studies.

EXAMPLE 10

Therapy of Relapsed or Refractory Metastatic Prostate Cancer

RhuMAb 2C4 is a full-length, humanized monoclonal antibody (produced in CHO cells) directed against ErbB2. RhuMab 2C4 blocks the associated of ErbB2 with other ErbB family members thereby inhibiting intracellular signaling through the ErbB pathway. In contrast to HERCEPTIN®, rhuMAb 2C4 not only inhibits the growth of ErbB2 overexpressing tumors but also blocks growth of tumors that require ErbB ligand-dependent signaling.

RhuMAb 2C4 is indicated as a single agent for treatment of hormone-refractory (androgen independent) prostate cancer patients. Primary endpoints for efficacy include overall survival compared to best available care (Mitoxantrone/Prednisone), when used as a single agent, and safety. Secondary efficacy endpoints include: time to disease progression, response rate, quality of life, pain and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of hormone-refractory (androgen independent) prostate cancer patients. Primary endpoints for efficacy include overall survival compared to chemotherapy, and safety. Secondary efficacy endpoints include: time to disease progression, response rate, quality of life, pain and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of drugs that can be combined with the anti-ErbB2 antibody (which blocks ligand activation of an ErbB2 receptor) to treat prostate cancer (e.g. androgen independent prostate cancer) include a farnesyl transferase inhibitor; an anti-angiogenic agent (e.g. an anti-VEGF antibody); an EGFR-targeted drug (e.g. C225 or ZD1839); another anti-ErbB2 antibody (e.g. a growth inhibitory anti-ErbB2 antibody such as HERCEPTIN®, or an anti-ErbB2 antibody which induces apoptosis such as 7C2 or 7F3, including humanized and/or affinity matured variants thereof); a cytokine (e.g. IL-2, IL-12. G-CSF or GM-CSF); an anti-androgen (such as flutamide or cyproterone acetate); leuprolide; suramin; a chemotherapeutic agent such as vinblastine, estramustine, mitoxantrone, liarozole (a retinoic acid metabolism-blocking agent), cyclophosphamide, anthracycline antibiotics such as doxorubicin, a taxane (e.g. paclitaxel or docetaxel), or methotrexate, or any combination of the above, such as vinblastine/estramustine or cyclophosphamide/doxorubicin/methotrexate; prednisone; hydrocortizone; or combinations thereof. Standard doses for these various drugs can be administered, e.g. 40 mg/m$^2$/wk docetaxel (TAXOTERE®); 6 (AUC) carboplatin; and 200 mg/m$^2$ paclitaxel (TAXOL®).

EXAMPLE 11

Therapy of Metastatic Breast Cancer

RhuMAb 2C4 is indicated as a single agent for treatment of metastatic breast cancer patients whose tumors do not overexpress ErbB2. Primary endpoints for efficacy include response rate and safety. Secondary efficacy endpoints include: overall survival, time to disease progression, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of metastatic breast cancer patients whose tumors do not overexpress ErbB2. Primary endpoints for efficacy include overall survival compared to chemotherapy alone, and safety. Secondary efficacy endpoints include: time to disease progression, response rate, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of drugs that can be combined with the anti-ErbB2 antibody (which blocks ligand activation of an ErbB2 receptor) to treat breast cancer (e.g. metastatic breast cancer which is not characterized by ErbB2 overexpression) include chemotherapeutic agents such as anthracycline antibiotics (e.g. doxorubicin), cyclophosphomide, a taxane (e.g. paclitaxel or docetaxel), navelbine, xeloda, mitomycin C, a platinum compound, oxaliplatin, gemcitabine, or combinations of two or more of these such as doxorubicin/cyclophosphomide; another anti-ErbB2 antibody (e.g. a growth inhibitory anti-ErbB2 antibody such as HERCEPTIN®, or an anti-ErbB2 antibody which induces apoptosis such as 7C2 or 7F3, including humanized or affinity matured variants thereof); an anti-estrogen (e.g. tamoxifen); a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); or combinations of the above. Standard dosages for such additional drugs may be used.

RhuMAb 2C4 is additionally indicated in combination with HERCEPTIN® for treatment of metastatic breast cancer patients whose tumors overexpress ErbB2. Primary endpoints for efficacy include response rate, and safety. Secondary efficacy endpoints include: time to disease progression, overall survival compared to HERCEPTIN® alone, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration). HERCEPTIN® is administered IV as an initial loading dose of 4 mg/kg followed by a weekly maintenance dose of 2 mg/kg. HERCEPTIN® is supplied as a lyophilized powder. Each vial of HERCEPTIN® contains 440 mg HERCEPTIN®, 9.9 mg L-histidine HCl, 6.4 mg L-histidine, 400 mg α-α-trehalose dihydrate, and 1.8 mg polysorbate 20. Reconstitution with 20 mL of Bacteriostatic Water for Injection (BWFI) containing 1.1% benzyl alcohol as a preservative, yields 21 mL of a multi-dose solution containing 21 mg/mL HERCEPTIN®, at a pH of approximately 6.0.

EXAMPLE 12

Therapy of Lung Cancer

RhuMAb 2C4 is indicated as a single agent for treatment of stage IIIb or IV non-small cell lung cancer (NSCLC). Primary endpoints for efficacy include response rate, and safety. Secondary efficacy endpoints include: overall survival, time to disease progression, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of metastatic non-small cell lung cancer patients. Primary endpoints for efficacy include overall survival compared to standard therapy, and safety. Secondary efficacy endpoints include: time to disease progression, response rate, quality of life and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of additional drugs which can be combined with the antibody (which binds ErbB2 and blocks ligand activation of an ErbB receptor) to treat lung cancer, include chemotherapeutic agents such as carboplatin, a taxane (e.g. paclitaxel or docetaxel), gemcitabine, navelbine, cisplatin, oxaliplatin, or combinations of any of these such as carboplatin/docetaxel; another anti-ErbB2 antibody (e.g. a growth inhibitory anti-ErbB2 antibody such as HERCEPTIN®, or an anti-ErbB2 antibody which induces apoptosis such as 7C2 or 7F3, including humanized or affinity matured variants thereof); a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); or combinations of the above.

EXAMPLE 13

Therapy or Colorectal Cancer

RhuMAb 2C4 is indicated as a single agent for treatment of metastatic colorectal cancer. Primary endpoints for efficacy include response rate and safety. Secondary efficacy endpoints include: overall survival, time to disease progression, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of metastatic colorectal cancer patients. Primary endpoints for efficacy include overall survival compared to standard therapy, and safety. Secondary efficacy endpoints include: time to disease progression, response rate, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of chemotherapeutic agents used to treat colorectal cancer, which can be combined with the antibody which binds ErbB2 and blocks ligand activation of an ErbB receptor, include 5-fluorouracil (5-FU), leucovorin (LV), CPT-11, levamisole, or combinations of any two or more of these, e.g., 5-FU/LV/CPT-11. Standard dosages of such chemotherapeutic agents can be administered. Other drugs that may be combined with the anti-ErbB2 antibody to treat colorectal cancer include a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); another anti-ErbB2 antibody (e.g. a growth inhibitory anti-ErbB2 antibody such as HERCEPTIN®, or an anti-ErbB2 antibody which induces apoptosis such as 7C2 or 7F3, including humanized or affinity matured variants thereof); or combinations of the above.

What is claimed is:

1. A method of treating cancer in a human, wherein the cancer expresses epidermal growth factor receptor (EGFR) and ErbB2, comprising administering to the human a therapeutically effective amount of an antibody which binds ErbB2 and blocks by 50% or greater binding of monoclonal antibody 2C4 (ATCC HB-12697) to ErbB2.

2. The method of claim 1 wherein the antibody blocks ligand activation of an ErbB receptor.

3. The method of claim 1 wherein the cancer is characterized by excessive activation of EGFR.

4. The method of claim 3 wherein the cancer overexpresses an ErbB ligand.

5. The method of claim, 5 wherein the ErbB ligand is transforming growth factor alpha (TGF-α).

6. The method of claim 1 wherein the antibody blocks TGF-α activation of mitogen-activated protein kinase (MAPK).

7. The method of claim 1 wherein the cancer is not characterized by overexpression of ErbB2 receptor.

8. The method of claim 1 wherein the cancer is selected from the group consisting of colon, rectal and colorectal cancer.

9. The method of claim 1 wherein the cancer is lung cancer.

10. The method of claim 9 wherein the cancer is non-small cell lung cancer.

11. The method of claim 1 wherein the antibody has a biological characteristic of monoclonal antibody 2C4 (ATCC HB-12697).

12. The method of claim 1 wherein the antibody is an antibody fragment.

13. The method of claim 12 wherein the antibody fragment is a Fab fragment.

14. The method of claim 1 wherein the antibody is not conjugated with a cytotoxic agent.

15. The method of claim 12 wherein the antibody fragment is not conjugated with a cytotoxic agent.

16. The method of claim 1 wherein the antibody is conjugated with a cytotoxic agent.

17. The method of claim 1 comprising administering at least one dose of the antibody to the human in an amount from about 0.5 mg/kg to about 10 mg/kg.

18. The method of claim 17 comprising administering the dose about every week.

19. The method of claim 17 comprising administering the dose about every three weeks.

20. A method of treating cancer in a human, wherein the cancer expresses but does not overexpress ErbB2 receptor, comprising administering to the human a therapeutically effective amount of an antibody which binds to ErbB2 and blocks ligand activation of an ErbB receptor more effectively than humanized monoclonal antibody huMAb4D5-8.

21. The method of claim 20 wherein the cancer is breast cancer.

22. The method of claim 21 wherein the cancer is metastatic breast cancer.

23. A method of treating cancer in a human, wherein the cancer is selected from the group consisting of colon, rectal and colorectal cancer which express but do not overexpress ErbB2, comprising administering to the human a therapeutically effective amount of an antibody which binds ErbB2 and blocks ligand activation of an ErbB receptor more effectively than humanized monoclonal antibody huMAb4D5-8.

24. A method of treating cancer in a human, wherein the cancer expresses epidermal growth factor receptor (EGFR) and ErbB2, comprising administering to the human a therapeutically effective amount of a humanized form of monoclonal antibody 2C4 (ATCC HB-12697).

* * * * *

UNITED STATES PATENT AND TRADEMARK OFFICE
CERTIFICATE OF CORRECTION

PATENT NO. : 6,949,245 B1
DATED : September 27, 2005
INVENTOR(S) : Mark Sliwkowski It is certified that error appears in the above-identified patent and that said Letters Patent is hereby corrected as shown below:

Column 75,
Line 50, please delete "claim, 5" and insert -- claim 4 --.

Signed and Sealed this

Sixth Day of December, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,949,245 B1 | Page 1 of 1 |
| APPLICATION NO. | : 09/602812 | |
| DATED | : September 27, 2005 | |
| INVENTOR(S) | : Sliwkowski | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this
Eighteenth Day of September, 2012

David J. Kappos
*Director of the United States Patent and Trademark Office*

SEQUENCE LISTING

```
<160> NUMBER OF SEQ ID NOS: 13

<210> SEQ ID NO 1
<211> LENGTH: 107
<212> TYPE: PRT
<213> ORGANISM: Mus Musculus

<400> SEQUENCE: 1

Asp Thr Val Met Thr Gln Ser His Lys Ile Met Ser Thr Ser Val
  1               5                  10                  15

Gly Asp Arg Val Ser Ile Thr Cys Lys Ala Ser Gln Asp Val Ser
                 20                  25                  30

Ile Gly Val Ala Trp Tyr Gln Gln Arg Pro Gly Gln Ser Pro Lys
                 35                  40                  45

Leu Leu Ile Tyr Ser Ala Ser Tyr Arg Tyr Thr Gly Val Pro Asp
                 50                  55                  60

Arg Phe Thr Gly Ser Gly Ser Gly Thr Asp Phe Thr Phe Thr Ile
                 65                  70                  75

Ser Ser Val Gln Ala Glu Asp Leu Ala Val Tyr Tyr Cys Gln Gln
                 80                  85                  90

Tyr Tyr Ile Tyr Pro Tyr Thr Phe Gly Gly Gly Thr Lys Leu Glu
                 95                 100                 105

Ile Lys

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Pro Glu Leu Val Lys Pro Gly
  1               5                  10                  15

Thr Ser Val Lys Ile Ser Cys Lys Ala Ser Gly Phe Thr Phe Thr
                 20                  25                  30

Asp Tyr Thr Met Asp Trp Val Lys Gln Ser His Gly Lys Ser Leu
                 35                  40                  45

Glu Trp Ile Gly Asp Val Asn Pro Asn Ser Gly Gly Ser Ile Tyr
                 50                  55                  60

Asn Gln Arg Phe Lys Gly Lys Ala Ser Leu Thr Val Asp Arg Ser
                 65                  70                  75

Ser Arg Ile Val Tyr Met Glu Leu Arg Ser Leu Thr Phe Glu Asp
                 80                  85                  90
```

-continued

```
Thr Ala Val Tyr Tyr Cys Ala Arg Asn Leu Gly Pro Ser Phe Tyr
            95                 100                 105

Phe Asp Tyr Trp Gly Gln Gly Thr Thr Leu Thr Val Ser Ser
            110                 115

<210> SEQ ID NO 3
<211> LENGTH: 107
<212> TYPE: PRT
<213> ORGANISM: Artificial sequence
<220> FEATURE:
<223> OTHER INFORMATION: humanized VL sequence

<400> SEQUENCE: 3

Asp Ile Gln Met Thr Gln Ser Pro Ser Ser Leu Ser Ala Ser Val
  1               5                  10                  15

Gly Asp Arg Val Thr Ile Thr Cys Lys Ala Ser Gln Asp Val Ser
                 20                  25                  30

Ile Gly Val Ala Trp Tyr Gln Gln Lys Pro Gly Lys Ala Pro Lys
                 35                  40                  45

Leu Leu Ile Tyr Ser Ala Ser Tyr Arg Tyr Thr Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Tyr Tyr Ile Tyr Pro Tyr Thr Phe Gly Gln Gly Thr Lys Val Glu
                 95                 100                 105

Ile Lys

<210> SEQ ID NO 4
<211> LENGTH: 119
<212> TYPE: PRT
<213> ORGANISM: Artificial sequence
<220> FEATURE:
<223> OTHER INFORMATION: Humanized VH sequence

<400> SEQUENCE: 4

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
                 20                  25                  30

Asp Tyr Thr Met Asp Trp Val Arg Gln Ala Pro Gly Lys Gly Leu
                 35                  40                  45

Glu Trp Val Ala Asp Val Asn Pro Asn Ser Gly Gly Ser Ile Tyr
                 50                  55                  60

Asn Gln Arg Phe Lys Gly Arg Phe Thr Leu Ser Val Asp Arg Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asn Leu Gly Pro Ser Phe Tyr
                 95                 100                 105

Phe Asp Tyr Trp Gly Gln Gly Thr Leu Val Thr Val Ser Ser
                 110                 115

<210> SEQ ID NO 5
<211> LENGTH: 107
<212> TYPE: PRT
<213> ORGANISM: Artificial sequence
```

```
<220> FEATURE:
<223> OTHER INFORMATION: light chain consensus sequence

<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
            95                  100                 105

Ile Lys

<210> SEQ ID NO 6
<211> LENGTH: 119
<212> TYPE: PRT
<213> ORGANISM: Artificial sequence
<220> FEATURE:
<223> OTHER INFORMATION: heavy chain consensus sequence

<400> SEQUENCE: 6

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
            35                  40                  45

Glu Trp Val Ala Val Ile Ser Gly Asp Gly Gly Ser Thr Tyr Tyr
        50                  55                  60

Ala Asp Ser Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
            95                  100                 105

Tyr Asp Tyr Trp Gly Gln Gly Thr Leu Val Thr Val Ser Ser
        110                 115

<210> SEQ ID NO 7
<211> LENGTH: 10
<212> TYPE: PRT
<213> ORGANISM: Mus musculus
<220> FEATURE:
<221> NAME/KEY: unsure
<222> LOCATION: 10
<223> OTHER INFORMATION: unknown amino acid

<400> SEQUENCE: 7

Gly Phe Thr Phe Thr Asp Tyr Thr Met Xaa
 1               5                  10

<210> SEQ ID NO 8
```

```
<211> LENGTH: 17
<212> TYPE: PRT
<213> ORGANISM: Mus musculus

<400> SEQUENCE: 8

Asp Val Asn Pro Asn Ser Gly Gly Ser Ile Tyr Asn Gln Arg Phe
1               5                   10                  15
Lys Gly

<210> SEQ ID NO 9
<211> LENGTH: 10
<212> TYPE: PRT
<213> ORGANISM: Mus musculus

<400> SEQUENCE: 9

Asn Leu Gly Pro Ser Phe Tyr Phe Asp Tyr
1               5                   10

<210> SEQ ID NO 10
<211> LENGTH: 11
<212> TYPE: PRT
<213> ORGANISM: Mus musculus

<400> SEQUENCE: 10

Lys Ala Ser Gln Asp Val Ser Ile Gly Val Ala
1               5                   10

<210> SEQ ID NO 11
<211> LENGTH: 7
<212> TYPE: PRT
<213> ORGANISM: Mus musculus
<220> FEATURE:
<221> NAME/KEY: unsure
<222> LOCATION: 5-7
<223> OTHER INFORMATION: unknown amino acid

<400> SEQUENCE: 11

Ser Ala Ser Tyr Xaa Xaa Xaa
1               5

<210> SEQ ID NO 12
<211> LENGTH: 9
<212> TYPE: PRT
<213> ORGANISM: Mus musculus

<400> SEQUENCE: 12

Gln Gln Tyr Tyr Ile Tyr Pro Tyr Thr
1               5

<210> SEQ ID NO 13
<211> LENGTH: 645
<212> TYPE: PRT
<213> ORGANISM: Homo sapiens

<400> SEQUENCE: 13

Met Glu Leu Ala Ala Leu Cys Arg Trp Gly Leu Leu Leu Ala Leu
1               5                   10                  15

Leu Pro Pro Gly Ala Ala Ser Thr Gln Val Cys Thr Gly Thr Asp
                20                  25                  30

Met Lys Leu Arg Leu Pro Ala Ser Pro Glu Thr His Leu Asp Met
                35                  40                  45

Leu Arg His Leu Tyr Gln Gly Cys Gln Val Val Gln Gly Asn Leu
                50                  55                  60
```

-continued

```
Glu Leu Thr Tyr Leu Pro Thr Asn Ala Ser Leu Ser Phe Leu Gln
             65                  70                  75

Asp Ile Gln Glu Val Gln Gly Tyr Val Leu Ile Ala His Asn Gln
             80                  85                  90

Val Arg Gln Val Pro Leu Gln Arg Leu Arg Ile Val Arg Gly Thr
             95                 100                 105

Gln Leu Phe Glu Asp Asn Tyr Ala Leu Ala Val Leu Asp Asn Gly
            110                 115                 120

Asp Pro Leu Asn Asn Thr Thr Pro Val Thr Gly Ala Ser Pro Gly
            125                 130                 135

Gly Leu Arg Glu Leu Gln Leu Arg Ser Leu Thr Glu Ile Leu Lys
            140                 145                 150

Gly Gly Val Leu Ile Gln Arg Asn Pro Gln Leu Cys Tyr Gln Asp
            155                 160                 165

Thr Ile Leu Trp Lys Asp Ile Phe His Lys Asn Asn Gln Leu Ala
            170                 175                 180

Leu Thr Leu Ile Asp Thr Asn Arg Ser Arg Ala Cys His Pro Cys
            185                 190                 195

Ser Pro Met Cys Lys Gly Ser Arg Cys Trp Gly Glu Ser Ser Glu
            200                 205                 210

Asp Cys Gln Ser Leu Thr Arg Thr Val Cys Ala Gly Gly Cys Ala
            215                 220                 225

Arg Cys Lys Gly Pro Leu Pro Thr Asp Cys Cys His Glu Gln Cys
            230                 235                 240

Ala Ala Gly Cys Thr Gly Pro Lys His Ser Asp Cys Leu Ala Cys
            245                 250                 255

Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro
            275                 280                 285

Glu Gly Arg Tyr Thr Phe Gly Ala Ser Cys Val Thr Ala Cys Pro
            290                 295                 300

Tyr Asn Tyr Leu Ser Thr Asp Val Gly Ser Cys Thr Leu Val Cys
            305                 310                 315

Pro Leu His Asn Gln Glu Val Thr Ala Glu Asp Gly Thr Gln Arg
            320                 325                 330

Cys Glu Lys Cys Ser Lys Pro Cys Ala Arg Val Cys Tyr Gly Leu
            335                 340                 345

Gly Met Glu His Leu Arg Glu Val Arg Ala Val Thr Ser Ala Asn
            350                 355                 360

Ile Gln Glu Phe Ala Gly Cys Lys Lys Ile Phe Gly Ser Leu Ala
            365                 370                 375

Phe Leu Pro Glu Ser Phe Asp Gly Asp Pro Ala Ser Asn Thr Ala
            380                 385                 390

Pro Leu Gln Pro Glu Gln Leu Gln Val Phe Glu Thr Leu Glu Glu
            395                 400                 405

Ile Thr Gly Tyr Leu Tyr Ile Ser Ala Trp Pro Asp Ser Leu Pro
            410                 415                 420

Asp Leu Ser Val Phe Gln Asn Leu Gln Val Ile Arg Gly Arg Ile
            425                 430                 435

Leu His Asn Gly Ala Tyr Ser Leu Thr Leu Gln Gly Leu Gly Ile
            440                 445                 450
```

-continued

```
Ser Trp Leu Gly Leu Arg Ser Leu Arg Glu Leu Gly Ser Gly Leu
                455                 460                 465

Ala Leu Ile His His Asn Thr His Leu Cys Phe Val His Thr Val
                470                 475                 480

Pro Trp Asp Gln Leu Phe Arg Asn Pro His Gln Ala Leu Leu His
                485                 490                 495

Thr Ala Asn Arg Pro Glu Asp Glu Cys Val Gly Glu Gly Leu Ala
                500                 505                 510

Cys His Gln Leu Cys Ala Arg Gly His Cys Trp Gly Pro Gly Pro
                515                 520                 525

Thr Gln Cys Val Asn Cys Ser Gln Phe Leu Arg Gly Gln Glu Cys
                530                 535                 540

Val Glu Glu Cys Arg Val Leu Gln Gly Leu Pro Arg Glu Tyr Val
                545                 550                 555

Asn Ala Arg His Cys Leu Pro Cys His Pro Glu Cys Gln Pro Gln
                560                 565                 570

Asn Gly Ser Val Thr Cys Phe Gly Pro Glu Ala Asp Gln Cys Val
                575                 580                 585

Ala Cys Ala His Tyr Lys Asp Pro Pro Phe Cys Val Ala Arg Cys
                590                 595                 600

Pro Ser Gly Val Lys Pro Asp Leu Ser Tyr Met Pro Ile Trp Lys
                605                 610                 615

Phe Pro Asp Glu Glu Gly Ala Cys Gln Pro Cys Pro Ile Asn Cys
                620                 625                 630

Thr His Ser Cys Val Asp Leu Asp Asp Lys Gly Cys Pro Ala Glu
                635                 640                 645
```